United States Patent
Venkataramanan et al.

(10) Patent No.: US 9,671,516 B2
(45) Date of Patent: Jun. 6, 2017

(54) MODIFIED PULSE SEQUENCE TO ESTIMATE PROPERTIES

(75) Inventors: Lalitha Venkataramanan, Lexington, MA (US); Tarek M. Habashy, Burlington, MA (US); Denise E. Freed, Newton Highlands, MA (US)

(73) Assignee: SCHLUMBERGER TECHNOLOGY CORPORATION, Cambridge, MA (US)

( * ) Notice: Subject to any disclaimer, the term of this patent is extended or adjusted under 35 U.S.C. 154(b) by 0 days.

(21) Appl. No.: 13/543,393

(22) Filed: Jul. 6, 2012

(65) Prior Publication Data

US 2013/0002246 A1    Jan. 3, 2013

Related U.S. Application Data

(63) Continuation of application No. 12/717,512, filed on Mar. 4, 2010, now Pat. No. 8,587,302.

(51) Int. Cl.
| | |
|---|---|
| *G01V 3/32* | (2006.01) |
| *G01V 3/14* | (2006.01) |
| *G01N 11/16* | (2006.01) |
| *G01R 33/44* | (2006.01) |

(52) U.S. Cl.
CPC ............ *G01V 3/14* (2013.01); *G01V 3/32* (2013.01); *G01N 11/16* (2013.01); *G01R 33/448* (2013.01)

(58) Field of Classification Search
CPC . G01V 3/14; G01V 3/32; G01N 11/16; G01R 33/448
USPC ....................................................... 324/303
See application file for complete search history.

(56) References Cited

U.S. PATENT DOCUMENTS

| | | | | |
|---|---|---|---|---|
| 5,343,151 | A * | 8/1994 | Cory | G01R 33/3875 324/319 |
| 5,486,762 | A | 1/1996 | Freedman et al. | |
| 6,005,389 | A | 12/1999 | Prammer | |
| 6,479,994 | B1 * | 11/2002 | Hills | G01N 24/085 324/303 |
| 6,600,316 | B2 | 7/2003 | Chen et al. | |
| 6,891,369 | B2 * | 5/2005 | Hurlimann et al. | 324/303 |
| 7,049,815 | B2 | 5/2006 | Itskovich et al. | |
| 7,301,339 | B1 * | 11/2007 | Cheng et al. | 324/303 |
| 7,305,306 | B2 | 12/2007 | Venkataramanan et al. | |
| 7,622,919 | B2 * | 11/2009 | Song | G01N 24/081 324/307 |
| 7,804,296 | B2 | 9/2010 | Flaum et al. | |

(Continued)

OTHER PUBLICATIONS

International Search Report and Written Opinion of PCT Application No. PCT/US2011/026008 dated Nov. 24, 2011: pp. 1-8.

(Continued)

*Primary Examiner* — Dixomara Vargas

(57) ABSTRACT

Methods and related systems are described for estimating fluid or rock properties from NMR measurements. A modified pulse sequence is provided that can directly provide moments of relaxation-time or diffusion distributions. This pulse sequence can be adapted to the desired moment of relaxation-time or diffusion coefficient. The data from this pulse sequence provides direct estimates of fluid properties such as average chain length and viscosity of a hydrocarbon. In comparison to the uniformly-spaced pulse sequence, these pulse sequences are faster and have a lower error bar in computing the fluid properties.

24 Claims, 14 Drawing Sheets

(56) References Cited

U.S. PATENT DOCUMENTS

| | | | | |
|---|---|---|---|---|
| 7,852,077 | B2* | 12/2010 | Song | G01N 24/081 324/309 |
| 8,965,094 | B2* | 2/2015 | Peacock, III | G01R 33/4625 128/922 |
| 9,140,769 | B2* | 9/2015 | van Zijl | G01R 33/5601 |
| 9,222,902 | B2* | 12/2015 | Gruber | G01N 24/081 |
| 2002/0105326 | A1 | 8/2002 | Hurlimann et al. | |
| 2005/0270023 | A1 | 12/2005 | Freedman | |
| 2006/0155472 | A1 | 7/2006 | Venkataramanan et al. | |
| 2008/0143330 | A1* | 6/2008 | Madio et al. | 324/303 |
| 2008/0314582 | A1 | 12/2008 | Belani et al. | |
| 2010/0043538 | A1* | 2/2010 | Cheng et al. | 73/54.42 |
| 2010/0259258 | A1 | 10/2010 | Fransson et al. | |

OTHER PUBLICATIONS

Allen et al., "How to Use Borehole Nuclear Magnetic Resonance," Oilfield Review, 1997: pp. 34-57.

Elshahawi et al., "SPE 100740: Combining Continuous Fluid Typing, Wireline Formation Testers, and Geochemical Measurements for an Improved Understanding of Reservoir Architecture," SPE Reservoir Evaluation & Engineering, Feb. 2008: pp. 27-40.

Fordham et al., "Imaging Multiexponential Relaxation in the (y, loge T1) Plane, with Application to Clay Filtration in Rock Cores," Journal of Magnetic Resonance Series A, 1995, vol. 113: pp. 139-150.

Freed, "Dependence on Chain Length of NMR Relaxation Times in Mixtures of Alkanes," Journal of Chemical Physics, 2007, vol. 126: pp. 174502-1-174502-10.

Freed et al., "Scaling Laws for Diffusion Coefficients in Mixtures of Alkanes," Physical Review Letters, Feb. 2005, vol. 94: pp. 067602-1-067602-4.

Hürlimann et al., "Quantitative Measurement of Two-Dimensional Distribution Functions of Diffusion and Relaxation in Grossly Inhomogeneous Fields," Journal of Magnetic Resonance, 2002, vol. 157: pp. 31-42.

Hürlimann et al., "Hydrocarbon Composition From NMR Diffusion and Relaxation Data," SPWLA 49th Annual Logging Symposium, May 2008: pp. 1-14.

Kleinberg et al., "SPE 26470: Nuclear Magnetic Resonance of Rocks: T1 vs. T2," SPE International, 1993: pp. 553-563.

Press et al., "Linear Regularization Methods," Numerical Recipes in C: The Art of Scientific Computing, Second Edition, New York: Cambridge University Press, 1992: 808-815.

Song et al., "T1-T2 Correlation Spectra Obtained Using a Fast Two-Dimensional Laplace Inversion," Journal of Magnetic Resonance, 2002, vol. 154: pp. 261-268.

Song et al., "Determining the resolution of laplace inversion spectrum," The Journal of Chemical Physics, 2005, vol. 122: pp. 104104-1-104104-8.

Venkataramanan et al., "Solving Fredholm Integrals of the First Kind With Tensor Product Structure in 2 and 2.5 Dimensions," IEEE Transactions on Signal Processing, May 2002, vol. 50(5): pp. 1017-1026.

GB Examination Report for corresponding GB Application Serial No. GB1205890.5, dated May 6, 2015, 3 pp.

* cited by examiner

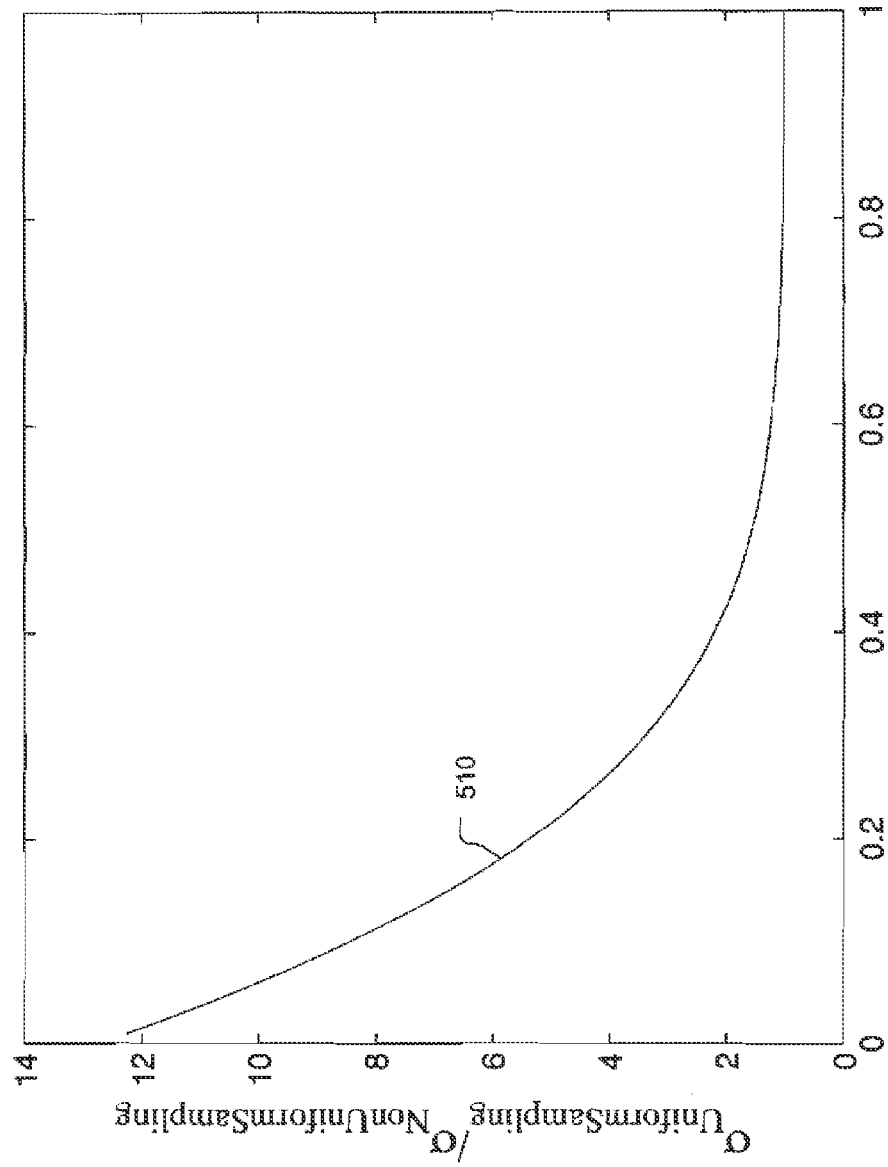

MODIFIED PULSE SEQUENCE TO ESTIMATE PROPERTIES

PRIORITY

This application claims priority as a continuation application of U.S. patent application Ser. No. 12/717,512 filed Mar. 4, 2010, with the same title as this application, which is incorporated by reference herein in its entirety. This continuation application contains the contents of U.S. Patent Application Ser. No. 60/242,218, filed on Sep. 14, 2009, which was incorporated by reference into the originally filed Ser. No. 12/717,512 application.

BACKGROUND

1. Field

This patent specification relates to estimating properties from exponentially decaying data. More particularly, this patent specification relates to methods and systems for estimating material properties from a non-uniform sequence of excitations, such as with NMR measurements.

2. Background

Traditionally, fluid properties using Nuclear Magnetic Resonance (NMR) are obtained by study of longitudinal or transverse relaxation or diffusion measurements. Longitudinal ($T_1$) relaxation data are acquired using an inversion-recovery pulse sequence where the recovery times are often chosen arbitrarily. Transverse ($T_2$) relaxation data are acquired using the CPMG pulse sequence with pulses that are typically uniformly spaced in the time-domain. There is no clear mathematical methodology for choosing the acquisition times at which the diffusion measurements are obtained. The relaxation or diffusion data thus obtained from these pulse sequences are used to infer the relaxation time or diffusion distributions. In turn, these distributions are used to infer petrophysical or hydrocarbon properties.

Traditional well-logging using NMR is employed to infer petro-physical and fluid properties of the formation or in-situ hydrocarbon. The multi-exponential time-decay of NMR magnetization is characterized by relaxation time constants $T_1$, $T_2$ or diffusion D and corresponding amplitudes $f_{T_1}(T_1)$, $f_{T_2}(T_2)$ or $f_D(D)$. Since the relaxation times and/or diffusion constants are expected to be continuous and typically span several decades, these amplitudes are often referred to as relaxation-time or diffusion distributions. These distributions provide a wealth of information about both the rock as well as fluid properties. See e.g. D. Allen, S. Crary, and R. Freedman, *How to use borehole Nuclear Magnetic Resonance*, Oilfield Review, pages 34-57, 1997.

An NMR measurement consists of a sequence of transverse magnetic pulses transmitted by an antenna. Typically, the CPMG pulse sequence is used to measure $T_2$ relaxation. It consists of a pulse that tips hydrogen protons 90° and is followed by several thousand pulses that refocus the protons by tipping them 180°. The data are acquired by an antenna between the evenly spaced 180° pulses and are thus uniformly spaced in time. On the other hand, the $T_1$ relaxation is studied using the inversion-recovery pulse sequence. There is no specific rule for choosing the recovery times. See, Y. Q. Song, L. Venkataramanan, and L. Burcaw, *Determining the resolution of Laplace inversion spectrum*, Journal of Chemical Physics, page 104104, 2005. Similarly, there is no clear mathematical framework to optimally choose the acquisition times for diffusion measurements.

The data acquired from all of the above pulse sequences can be represented by a Fredholm integral (see, M. D. Hurlimann and L. Venkataramanan, *Quantitative measurement of two dimensional distribution functions of diffusion and relaxation in grossly homogeneous fields*, Journal Magnetic Resonance, 157:31-42, July 2002 and L. Venkataramanan, Y. Q. Song, and M. D. Hurlimann, *Solving Fredholm integrals of the first kind with tensor product structure in 2 and 2.5 dimensions*, IEEE Transactions on Signal Processing, 50:1017-1026, 2002, hereinafter "Venkataramanan et al. 2002"), $$M(t) = \int_0^\infty e^{-t/x} f_x(x) \, dx \tag{1}$$

where the variable x typically refers to $T_1$, $T_2$, or $1/D$. See, Venkataramanan et al. 2002. Thus the measured data in eqn. (1) is related to a Laplace transform of the unknown underlying function $f_x(x)$.

Scaling laws established on mixtures of alkanes provide a relation between fluid composition and relaxation time and/or diffusion coefficients of the components of the mixture (see D. E. Freed, *Scaling laws for diffusion coefficients in mixtures of alkanes*, Physical Review Letters, 94:067602, 2005, and D. E. Freed, *Dependence on chain length of NMR relaxation times in mixtures of alkanes*, Journal of Chemical Physics, 126:174502, 2007). A typical crude oil has a number of components, such as methane, ethane etc. Let $N_i$ refer to the number of carbon atoms or chain length of the i-th component. Let $\overline{N}$ denote the molar average chain length of the crude oil, also defined as the harmonic mean of the chain lengths, $$\frac{1}{\overline{N}} \equiv \sum_{i=1}^\infty \frac{f_N(N_i)}{N_i} = \langle N^{-1} \rangle \tag{2}$$

where $f_N(N_i)$ denotes the mass fraction of component i in the hydrocarbon. According to the scaling law, the bulk relaxation time $T_{2,i}$ of component i in a crude oil follows a power law and depends inversely on its chain length or number of carbon atoms, $N_i$. Thus, the larger the molecule, the smaller the relaxation time $T_{2,i}$. The relaxation time also depends inversely on the average chain length $\overline{N}$ of the hydrocarbon, according to $$T_{2,i} = B N_i^{-\kappa} \overline{N}^{-\gamma} \tag{3}$$

In eqn. (3), parameters B, $\gamma$ and $\kappa$ are constants at a given pressure and temperature. Similarly, if $D_i$ refers to the diffusion coefficient of component i, $$D_i = A N_i^{-\nu} \overline{N}^{-\beta} \tag{4}$$

where A, $\nu$ and $\beta$ and are constants at a given pressure and temperature. The scaling theory can also be used to derive an expression for fluid viscosity, $$\eta \propto \langle D^{-1} \rangle \Rightarrow \eta \propto \overline{N}^\beta \langle N^\nu \rangle. \tag{5}$$

Traditional analysis of the measured NMR data to obtain fluid properties goes as follows. The inverse Laplace transform of eqn. (1) is performed to estimate the probability density function $f_x(x)$ from the measured data. Next, using eqns. (3)-(5), the average chain length $\overline{N}$ and the chain length distribution $f_N(N)$ are computed. Viscosity $\eta$ of the hydrocarbon is then estimated using eqn. (5). This traditional analysis has some disadvantages. First, the inverse Laplace transform of the measured NMR data in eqn. (1) is non-linear due to the non-negativity constraint on $f_x(x)$. See, Venkataramanan et al. 2002, and E. J. Fordham, A. Sezginer, and L. D. Hall, *Imaging multiexponential relaxation in the $(y, \log_e T_1)$ plane, with application to clay filtration in rock cores*, J. Mag. Resonance A, 113:139-150, 1995. Next, it is also mathematically ill-conditioned. Often, regularization or prior information about the expected solution is incorporated into the problem formulation to make it better conditioned. However, the choice of the regularization functional as well as the weight given to the prior information is a well-known drawback of this transform due to its non-uniqueness. See, W. H. Press, S. A. Teukolsky, and W. T. Vetterling, *Numerical Recipes in C*, Cambridge University Press, 1992. Thus errors in the estimation of $T_1$, $T_2$, or D distributions are propagated into errors in the estimation of fluid properties.

SUMMARY

According to some embodiments, a method for estimating a property of a material is provided. A measurable change in the material is induced and measurements are made of an aspect of the material that tends to exponentially decay following the induction. The induction is repeated at predetermined intervals, and the material property is estimated based on measurements of the aspect. The intervals are designed so as to improve the estimation of the property.

The induction can be a transmitted transverse magnetic pulse as with NMR measurements, according to some embodiments. According to some embodiments the induction is the induction of a pressure or temperature change in the material. According to some embodiments, the interval spacing (e.g. in time, in frequency, etc.) is designed according to a formula determined by the property being estimated, and the spacing is non-uniform in both linear and logarithmic scales. According to some embodiments the interval spacing in time follows a power law and allows for the material property to be directly computed from the measurements.

The method can be carried out as part of an oilfield service, and the measurements can be made downhole. The material can be a fluid, a solid or a mixture. According to some embodiments, the material is one or more rock solids and the material properties being estimated are petrophysical properties of the rock solids.

According to some embodiments, a system for estimating a property of a material is provided that includes an inducer that is adapted to induce a measurable change in the material, and one or more sensors adapted to measure an aspect of the material that tends to exponentially decay following an induction. A controller is coupled to the inducer, and adapted and programmed to repeat the induction at predetermined intervals. A processing system is adapted to estimate the material property based on measurements. The induction intervals are designed so as to improve the estimation of the property.

Further features and advantages will become more readily apparent from the following detailed description when taken in conjunction with the accompanying drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 5 is a plot showing the ratio of the error-bar in the moments obtained from uniform sampling to non-uniform sampling;

DETAILED DESCRIPTION OF THE PREFERRED EMBODIMENTS

Figure 1:
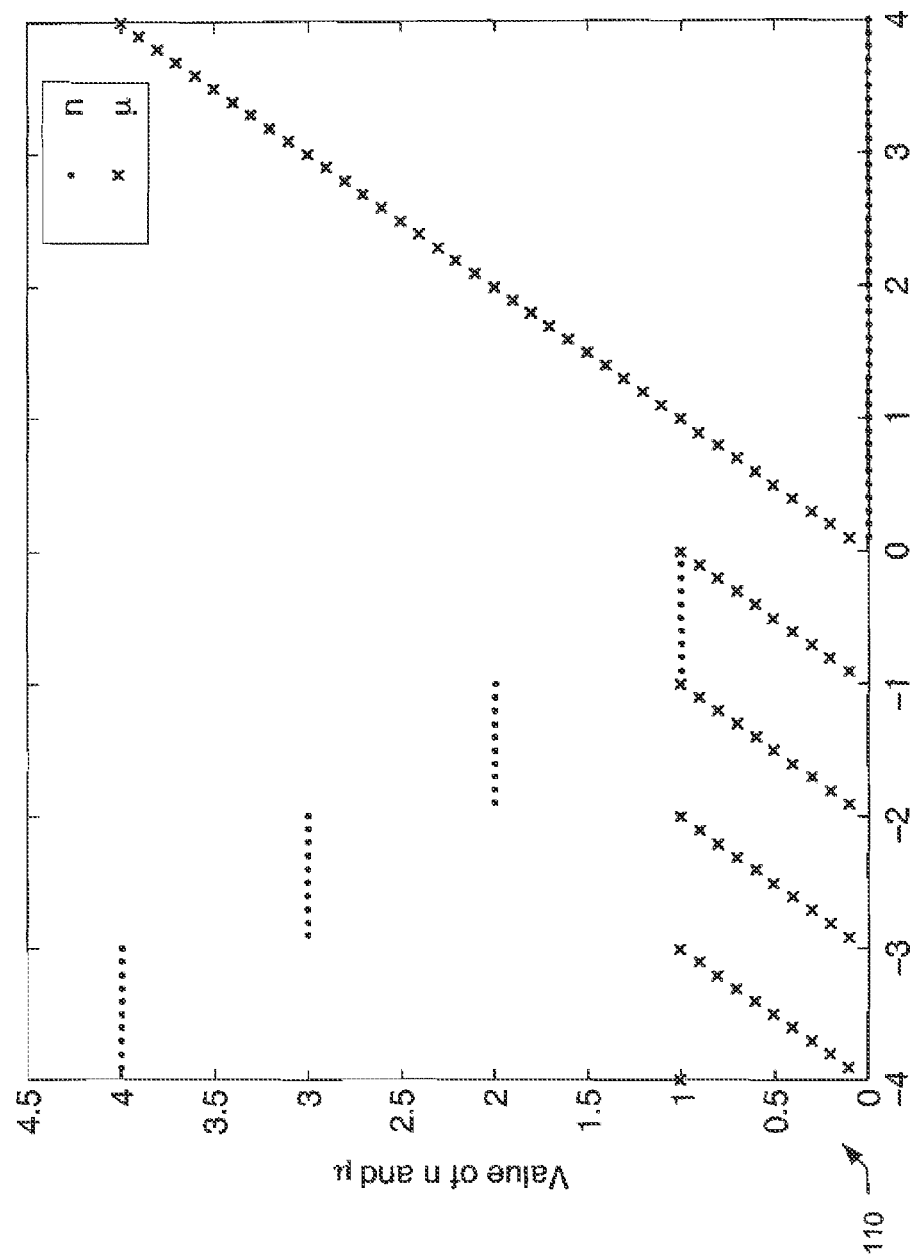
FIG. 1 is a plot showing the values of n and μ for different values of ω as determined by equation (8) herein.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, modified pulse sequences are provided that allow for the direct measurements of moments of relaxation-time or diffusion distributions. The data from these pulse sequences provides direct estimates of fluid properties such as average chain length and viscosity of a hydrocarbon. In comparison to the uniformly-spaced pulse sequence, these pulse sequences are faster and have a lower error bar in computing the fluid properties.

Co-pending U.S. Patent Application No. 61/242,218, filed Sep. 14, 2009 (incorporated herein by reference and copied below) describes a method to analyse NMR data that obviates the estimation of the $T_1$, $T_2$, or D distributions.

This invention relates to the field of estimation of sample properties. One preferred application of such scheme would be estimation of the properties of a sample from exponentially decaying data.

Fitting exponentials to measured data is a well-known ill-conditioned problem in science and engineering. It involves solving for non-negative amplitude with time constant $T_2$ and amplitudes $f_{T_2}$ from the measured multi-exponential decay M(t) in the time-domain:

$$M(t) = \int_0^\infty e^{-t/T_2} f_{T_2}(T_2) dT_2. \quad (1)$$

The time constants $T_2$ are often assumed to be a continuum. Without loss of generality, the corresponding non-negative amplitude $f_{T_2}$ is considered to be the probability density function of variable $T_2$.

Nuclear magnetic resonance (NMR) applications in biological systems, porous media or well-logging are further discussed hereinafter as exemplary applications comprising exponentially decaying data. However, the method of the invention relates to any type of exponentially decaying data.

Traditional well-logging using Nuclear Magnetic Resonance (NMR) is employed to infer petrophysical properties of the formation as well as in-situ fluid properties. The multi-exponential time-decay of NMR magnetization is characterized by relaxation times $T_1$ or $T_2$, and corresponding amplitudes $f_{T_1}(T_1)$ or $f_{T_2}(T_2)$ (See R. L. Kleinberg, C. Straley, W. E. Kenyon, R. Akkurt, and S. A. Farooqui. Nuclear magnetic resonance of rocks: T1 vs. T2. *SPE*, 26470:553-563, 1993). Often, the magnetization data has a wide range of relaxation times and $f_{T_1}(T_1)$ or $f_{T_2}(T_2)$ corresponds to a distribution of the underlying relaxation times.

These distributions provide information such as the range of pore-sizes in a rock and are empirically related to rock permeability. They are also used to distinguish bound fluid versus free-fluid in a rock. NMR relaxation measurements of bulk hydrocarbons are also used to infer oil viscosity. More recently, two-dimensional measurements, such as diffusion-relaxation, have been used to provide information about fluid typing and saturation (M. D. Hurlimann and L. Venkataramanan. Quantitative measurement of two dimensional distribution functions of diffusion and relaxation in grossly homogeneous fields. *Journal Magnetic Resonance*, 157:31-42, July 2002).

The core of the NMR interpretation relies on the inverse Laplace transform of the magnetization data to reconstruct $f_{T_1}(T_1)$ or $f_{T_2}(T_2)$. It is well-known that computation of this transform is a mathematically ill-conditioned problem (L. Venkataramanan, Y.-Q. Song, and M. D. Hurlimann. Solving Fredholm integrals of the first kind with tensor product structure in 2 and 2.5 dimensions. *IEEE Transactions on Signal Processing*, 50:1017-1026, 2002). Often, regularization or prior information about the expected solution needs to be incorporated to make the problem better conditioned. However, the choice of the regularization functional as well as the weight given to prior information is a well-known drawback of this transform due to its non-uniqueness.

In oilfield applications, the measured NMR magnetization data denoted by M(t) is a multiexponential decay, with time constant $T_2$ and amplitudes $f_{T_2}$.

The relaxation time $T_2$ is the characteristic time corresponding to loss of energy by protons in hydrocarbons or water present in pores of a rock or in the bulk fluid. There are a number of mechanisms for loss of this energy: frequent collision of molecules with the pore surface (surface relaxation), diffusion in a magnetic field (diffusion-induced relaxation) and interaction with other fluid molecules (bulk relaxation).

As seen in eqn. (1), the measured data M(t) is a Laplace transform of the amplitudes $f_{T_2}(T_2)$. Traditionally, the inverse Laplace transform is used to estimate the time constants $T_2$ and amplitudes $f_{T_2}(T_2)$ from the measured data. The time constants $T_2$ are often assumed to be a continuum; thus the corresponding amplitudes $f_{T_2}(T_2)$ are referred to as the $T_2$ distribution. The amplitude $f_{T_2}(T_2)$ at any given $T_2$ is proportional to the number of protons relaxing at that rate. Thus, the area under the $T_2$ distribution is interpreted as the porosity of the rock. Often, based on lithology, a threshold $T_2$ is chosen as the cut-off characteristic time separating fluid bound to the pore surface and fluid that is not bound to the pore surface and can flow more easily. For example, in sandstones, the area under the $T_2$ distribution corresponding to relaxation times smaller than 33 msec has been empirically related to bound fluid volume. The remaining area under the $T_2$ distribution corresponds to free fluid volume. The mean of the distribution, $\langle \ln(T_2) \rangle$ is empirically related to either rock permeability and/or to hydrocarbon viscosity. The width of the distribution, $\sigma_{\ln(T_2)}$ provides a qualitative range of the distribution of pore sizes in the rock. Similar answer products obtained from either areas or moments are computed from two-dimensional diffusion-relaxation data or $T_1$-$T_2$ relaxation data (See Y.-Q. Song, L. Venkataramanan, M. D. Hurlimann, M. Flaum, P. Frulla, and C. Straley. T1-T2 correlation spectra obtained using a fast two-dimensional Laplace inversion. *Journal Magnetic Resonance*, 154:1-8, 2002, and D. Allen, S. Crary, and R. Freedman. How to use borehole Nuclear Magnetic Resonance. *Oilfield Review*, pages 34-57, 1997).

Eqn. (1) provides the forward model for $T_2$ relaxation. Other pulse sequences used to measure petrophysical or fluid properties such as diffusion D or longitudinal relaxation $T_1$ result in mathematical formulations similar to eqn. (1), with the variable $T_2$ being replaced by relaxation $T_1$ or 1/D. Thus, analysis developed for solving eqn. (1) for $f_{T_2}(T_2)$ can also be used to solve for distributions of longitudinal relaxation $f_{T_1}(T_1)$ and diffusion $f_D(D)$.

It is well known in the literature that the inverse Laplace transform is an ill-conditioned problem. Small changes in the measured data due to noise can result in widely different $T_2$ distributions. In theory, there are infinitely many solutions for $f_{T_2}(T_2)$. In the literature, this problem is typically solved by subjectively choosing the "smoothest" solution $f_{T_2}(T_2)$ that fits the data. This smooth $T_2$ distribution is often estimated by minimization of a cost function Q with respect to the underlying $f$ (E. J. Fordham, A. Sezginer, and L. D. Hall. Imaging multiexponential relaxation in the (y, $\log_e T_1$) plane, with application to clay filtration in rock cores. *J. Mag. Resonance A*, 113:139-150, 1995), $$Q = \|M - Kf\|^2 + \alpha \|f\|^2, \tag{2}$$

where M is the measured data, K is the matrix of the discretized kernel $e^{-t/T_2}$ and $f$ is the discretized version of the underlying density function $f_{T_2}(T_2)$ in eqn. (1). The first term in the cost function is the least squares error between the data and the fit from the model in eqn. (1). The second term is referred to as regularization and incorporates smoothness in the relaxation amplitudes into the problem formulation. The parameter $\alpha$ denotes the compromise between the fit to the data and an a priori expectation of the distribution.

The use of regularization and incorporation of smoothness into the problem formulation is subjective. In eqn. (2), it is possible to define alternate cost functions based on entropy, the Backus-Gilbert method or other measures of difference between data and fit (W. H. Press, S. A. Teukolsky, and W. T. Vetterling. *Numerical Recipes in C*. Cambridge University Press, 1992). In the next section, we describe an alternate method that obviates the need for the use of the inverse Laplace transform and the computation of the $T_2$ distribution to estimate parameters such as $\langle \ln(T_2) \rangle$ and $\sigma_{\ln(T_2)}$.

An alternate method is described that operates directly on the measured magnetization data and provides information about a sample parameters without the need for this ill conditioned inverse Laplace transform.

Consider a function of the form:

$$G(\omega) \equiv \ln \langle T_2^\omega \rangle \tag{3}$$

where $\omega$ is a real number, $\langle . \rangle$ refers to the expectation operator and $\langle T_2^\omega \rangle$ refers to the expected value of the $\omega$-th moment of $T_2$, defined as $$\langle T_2^\omega \rangle \equiv \frac{\int_0^\infty T_2^\omega f_{T_2}(T_2) dT_2}{\int_0^\infty f_{T_2}(T_2) dT_2} = \frac{1}{\phi} \int_0^\infty T_2^\omega f_{T_2}(T_2) dT_2 \tag{4}$$

where $\phi$ is the porosity and $$\phi = M(t=0) = \int_0^\infty f_{T_2}(T_2) dT_2.$$

By construction, G( ) is the second characteristic function of $\ln(T_2)$ (see Appendix A), with $$\left.\frac{dG}{d\omega}\right|_{\omega=0} = \langle \ln(T_2) \rangle, \quad \left.\frac{d^2 G}{d\omega^2}\right|_{\omega=0} = \sigma_{\ln(T_2)}^2. \tag{5}$$

In eqn. (3), $G(\omega)$ can be computed from moments $\langle T_2^\omega \rangle$ of relaxation time $T_2$ which, in turn, can be computed directly from the measurement (see Appendix B), $$\langle T_2^\omega \rangle = \frac{(-1)^n}{\Gamma(\mu)\phi} \int_0^\infty t^{\mu-1} \left[\frac{d^n M(t)}{dt^n}\right] dt, \omega = \mu - n \tag{6}$$

where $\Gamma( )$ represents the Gamma function. The contribution of variable $\omega$ is in two parts: a real number $\mu$ and an integer n where the mathematical operator $t^{\mu-1}$ operates on the n-th derivative of the data. As shown in Appendix B, when $\omega > 0: n = 0, \mu = \omega$ $\omega \leq 0: \omega = \mu - n, \ 0 < \mu \leq 1, \ n = [-\omega] + 1.$  (7)

where $[\omega]$ refers to the integral part of the number $\omega$. In eqn. (1), the moments $\langle T_2^\omega \rangle$ are computed as a weighted linear combination of the measured data. This, in turn, allows easy computation of the function G( ) in eqn. (3) and thus, the parameters $\langle \ln(T_2) \rangle$ and $\sigma_{\ln(T_2)}$ in eqn. (5).

In another embodiment of the invention, the moments of relaxation time can also be calculated in the Fourier domain (see Appendix C).

Examples of Applications

In addition to direct computation of parameters such as $\langle \ln(T_2) \rangle$ and $\sigma_{\ln(T_2)}$, the computation of moments has numerous applications. Some of these applications are listed below.

1 Hydrocarbon Properties

We demonstrate below that the computation of moments of relaxation time is useful for example in the computation of hydrocarbon properties such as average chain length, viscosity and parameters relating fluid composition to NMR data.

Scaling laws established on mixtures of alkanes provide a relation between fluid composition and relaxation time and/or diffusion coefficients of the components of the mixture (See D. E. Freed. Scaling laws for diffusion coefficients in mixtures of alkanes. *Physical Review Letters*, 94:067602, 20058, and D. E. Freed. Dependence on chain length of NMR relaxation times in mixtures of alkanes. *Journal of Chemical Physics*, 126:174502, 2007). A typical crude oil has a number of components, such as methane, ethane etc. Let $N_i$ refer to the number of carbon atoms or the chain length of the i-th component. Let $\bar{N}$ denote the molar average chain length of the crude oil, defined as the harmonic mean of the chain lengths, $$\frac{1}{\bar{N}} \equiv \sum_{i=1}^\infty \frac{f_N(N_i)}{N_i} = \langle N^{-1} \rangle \tag{8}$$

where $f_N(N_i)$ denotes the mass fraction of component i in the hydrocarbon. According to the scaling law, the bulk relaxation time $T_{2,i}$ of component i in a crude oil follows a power law and depends inversely on its chain length or number of carbon atoms, $N_i$. Thus, the larger the molecule, the smaller the relaxation time $T_{2,i}$. The relaxation time also depends inversely on the average chain length $\overline{N}$ of the hydrocarbon, according to $$T_{2,i} = BN_i^{-\kappa}\overline{N}^{-\gamma}. \qquad (9)$$

In eqn. (9), parameters B, $\gamma$, $\kappa$ are constants at a given temperature and pressure. Similarly, if $D_i$ refers to the diffusion coefficient of component i $$D_i = AN_i^{-\nu}\overline{N}^{-\beta} \qquad (10)$$

where A, $\nu$, $\beta$ are constants at a given temperature and pressure. The scaling laws in eqns. (9) and (10) imply that measurements of diffusion or relaxation can be used to characterize fluid composition. The scaling theory can also be used to derive an expression for fluid viscosity, $$\eta \propto \langle D^{-1} \rangle \Rightarrow \eta \propto \overline{N}^{\beta}\langle N^\nu \rangle. \qquad (11)$$

Traditional analysis of NMR relaxation data to compute either the average chain length or viscosity involves the following steps. First, one of the infinitely many solutions for $f_{T_2}(T_2)$ is computed from eqn. (2). Next, the chain length distribution $f_N(N_i)$ is computed using eqn. (9). Next, fluid properties such as the average chain length and viscosity are computed using eqn. (11). Errors in the estimation of $f_{T_2}(T_2)$ from the ill-conditioned nature of the inverse Laplace transform are propagated into the estimation of fluid properties.

We show below that the computation of moments of either the relaxation times or diffusion constants allows direct estimation of the fluid properties. Taking the expectation operator on either side of Eqns. (9) and (10) and re-writing it, the average chain length from either the relaxation-time or diffusion data is $$\overline{N} = [B^{-1/\kappa}\langle T_2^{1/\kappa}\rangle]^{-\frac{\kappa}{\gamma+\kappa}} \qquad (12)$$

$$\overline{N} = [A^{-1/\nu}\langle D^{1/\nu}\rangle]^{-\frac{\nu}{\nu+\beta}}. \qquad (13)$$

From eqn. (11), the viscosity of the hydrocarbon can be computed directly from the moments of relaxation time, $$\eta \propto \left[\left\langle T_2^{\frac{1}{\kappa}}\right\rangle\right]^{\frac{\beta\kappa-\gamma\nu}{\gamma+\kappa}}\left\langle T_2^{-\frac{\nu}{\kappa}}\right\rangle. \qquad (14)$$

Thus, using eqns. (12) and (14) fluid properties such as average chain length and the fluid viscosity of a hydrocarbon can be computed directly from the moments of the relaxation time, which, in turn, can be directly computed from the data using eqns. (6) and (7). Similarly, eqns. (11) and (13) enable direct computation of fluid properties from diffusion data. In addition to characterizing the hydrocarbon, the average chain length can be a useful parameter to help classify hydrocarbons (M. D. Hurlimann, D. E. Freed, L. J. Zielinski, Y. Q. Song, G. Leu, C. Straley, C. Cao Minh, and A. Boyd. Hydrocarbon composition from NMR diffusion and relaxation data. *SPWLA 49th logging symposium,* 2008). The temperature independence of this parameter can also be used to identify changes in hydrocarbon properties with depth.

The parameters B, $\gamma$, $\kappa$ in eqn. (9) and A, $\nu$, $\beta$ in eqn. (10) relate relaxation times or diffusion coefficients to fluid composition in a mixture. Given NMR and gas-chromatography (GC) data, we show below that the computation of $G(\omega)$ provides a direct method to estimate these parameters in a crude oil. Taking the variance on either side of eqn. (9) yields $$\sigma_{\ln(T_2)}^2 = \kappa^2 \sigma_{\ln(N)}^2, \qquad (15)$$

where $\sigma_{\ln(T_2)}^2$ can be computed from NMR data using eqn. (5) and $\sigma_{\ln(N)}^2$ can be obtained from GC data which provides fluid composition. Thus, given NMR and GC data, $\kappa$ for any crude oil is obtained as the ratio of the width or standard deviation of the $T_2$ distribution to the width or standard deviation of the chain length distribution in the log-domain. The parameters B and $\gamma$ can be computed in a similar manner. Taking the expectation on either side of eqn. (9) yields $$\langle \ln(T_2)\rangle = \ln(B) - \gamma \ln(\overline{N}) - \kappa \langle \ln(N)\rangle. \qquad (16)$$

The term $\langle \ln(T_2)\rangle$ can be computed from NMR data using eqn. (5). Parameter $\kappa$ is found from eqn. (15). Parameters $\overline{N}$ and $\langle \ln(N)\rangle$ are computed from GC data. Thus, eqn. (16) is linear in parameters ln B and $\gamma$. Given data from two or more hydrocarbons with similar properties, these parameters can be estimated. When the data are measured as a function of temperature and pressure, parameters $\kappa$, B and $\gamma$ can be computed as a function of temperature and pressure. For example, from measured NMR and GC data, the value of $\kappa$ on various crude oils in the lab obtained using eqn. (15) are shown in Table 1. The error-bar in $\kappa$ is around 0.05.

TABLE I

Estimated $\kappa$ values from different crude oils

| Sample | 30 C. | 60 C. | 90 C. | 120 C. |
|---|---|---|---|---|
| 1 | 1.46 | 1.38 | 1.29 | 1.22 |
| 2 | 1.51 | 1.46 | 1.41 | N/A |
| 3 | 1.37 | 1.29 | 1.22 | 1.16 |
| 4 | 1.54 | 1.39 | 1.34 | 1.21 |

For a given sample, the magnitude of $\kappa$ seemingly decreases with increasing temperature. The value of $\kappa$ may also vary slightly from one sample to another. This may have an important implication in the computation of fluid composition from measured NMR data. Similar analysis holds good for estimated parameters A, $\nu$ and $\beta$ in eqn. (10). Given both gas-chromatography and NMR diffusion data, $$\sigma_{\ln(D)}^2 = \nu^2 \sigma_{\ln(N)}^2 \qquad (17)$$

$$\langle \ln(D)\rangle = \ln(A) - \beta \ln(\overline{N}) - \nu \langle \ln(N)\rangle. \qquad (18)$$

Thus, using eqns. (17) and (18), NMR diffusion and GC data can be used to the estimate the parameters A, $\nu$ and $\beta$ and study their variation with temperature and pressure.

2 Identification of Fluid Phase Change

An abrupt change in fluid parameters with temperature and pressure can be an indicator of fluid phase change such as wax or asphaltene precipitation. For example, Table 2 shows the value of estimated $\kappa$ with temperature for a particular lab sample. It is seen that above 30 C the value of $\kappa$ is around 1.4±0.1. Below 20 C, $\kappa$ increases abruptly to 1.7±0.1, indicating that the molecular dynamics has slowed, signaling a phase transition. In this lab example, wax was found to have precipitated in the hydrocarbon between 20 and 30 C. Thus monitoring the value of $\kappa$ (or other moments of relaxation time or diffusion such as the mean chain length) as a function of temperature or pressure can help identify abrupt changes in fluid properties indicating phase transitions.

TABLE 2

Estimated κ values from one crude oil at different temperatures indicates a phase transition between 20 and 30 C.

| Temperature (C.) | κ |
|---|---|
| 5 | 1.67 ± 0.1 |
| 10 | 1.67 ± 0.1 |
| 15 | 1.61 ± 0.1 |
| 20 | 1.75 ± 0.1 |
| 30 | 1.42 ± 0.01 |
| 50 | 1.30 ± 0.1 |

3 Computation of Error-Bars on Answer Products

The traditional analysis for computing $T_2$ distributions is intrinsically non-linear due to the non-negativity constraint on the distribution [3]. Thus, computation of error-bars has been a longstanding issue. Since the new analysis described in the previous section provides a linear and analytical expression for the parameters of interest, the error-bars are easily computed analytically. For example, when $\omega>0$, using eqns. (6) and (7), we have $$\sigma_{\langle T_2^\omega \rangle} = \frac{\sigma_\partial}{\Gamma(\omega)\phi} t_E^\omega \sqrt{\sum_{n=1}^{N_e} n^{2\omega-2}} \qquad (19)$$

where $\sigma_\epsilon$ is the standard deviation of additive white noise in the measurement, $N_e$ is the number of echoes in the measured $T_2$ relaxation data and $t_E$ is the echo spacing. Eqn. (19) provides an insight into the desired signal to noise ratio in the data required to produce a desired uncertainty in the computation of moments. In turn, this can be converted into uncertainty in the desired fluid and petrophysical parameters.

Computation of fluid properties along with associated uncertainty from NMR data can play a significant role in determining reservoir connectivity. Abrupt changes in fluid properties, such as fluid composition or viscosity between zones in a single well or between neighboring wells can, under some circumstances, be a marker for reservoir compartmentalization (See H. Elshahawi, L. Venkataramanan, D. McKinney, M. Flannery, O. C. Mullins, and M. Hashem. Combining continuous fluid typing, wireline formation testers, and geochemical measurements for an improved understanding of reservoir architecture. *SPE Reservoir Evaluation and Engineering*, pages 27-40, 2008). However, the abrupt differences in fluid properties can be identified reliably only when the significance of uncertainties is taken into account. Therefore, computation of fluid properties from NMR along with associated uncertainties can help determine if fluids in neighboring zones are statistically similar or different. If the two fluids in adjacent layers are statistically different, there may be a permeability barrier between the zones that divides the layer into separate flow-units.

Simulations

Figure 8:
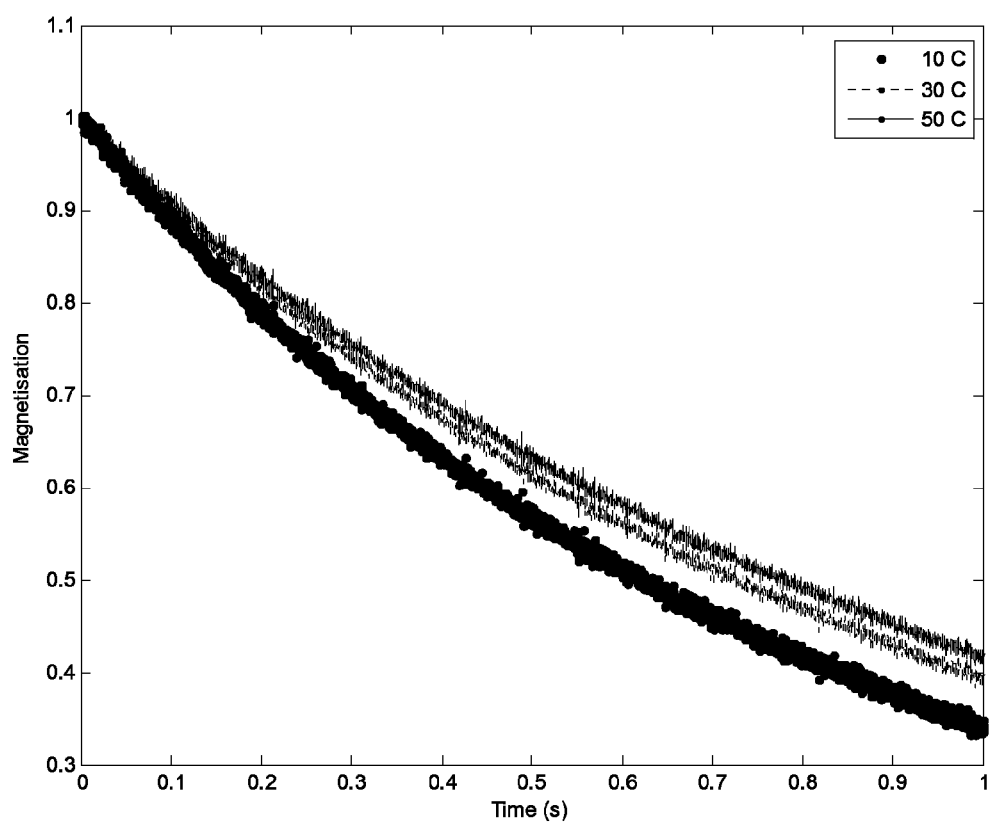
FIG. 8 represents magnetization data simulated with additive white noise with $\sigma_\epsilon = 0.01$ at three different temperatures.

In the first simulation, NMR data were simulated from gas-chromatography using eqn. (9) with a constant value of κ=1.24 at three temperatures: 10, 30 and 50 C. FIG. 8 shows one realization of data with additive white Gaussian noise with $\sigma_\epsilon$=0.01.

Figure 9:
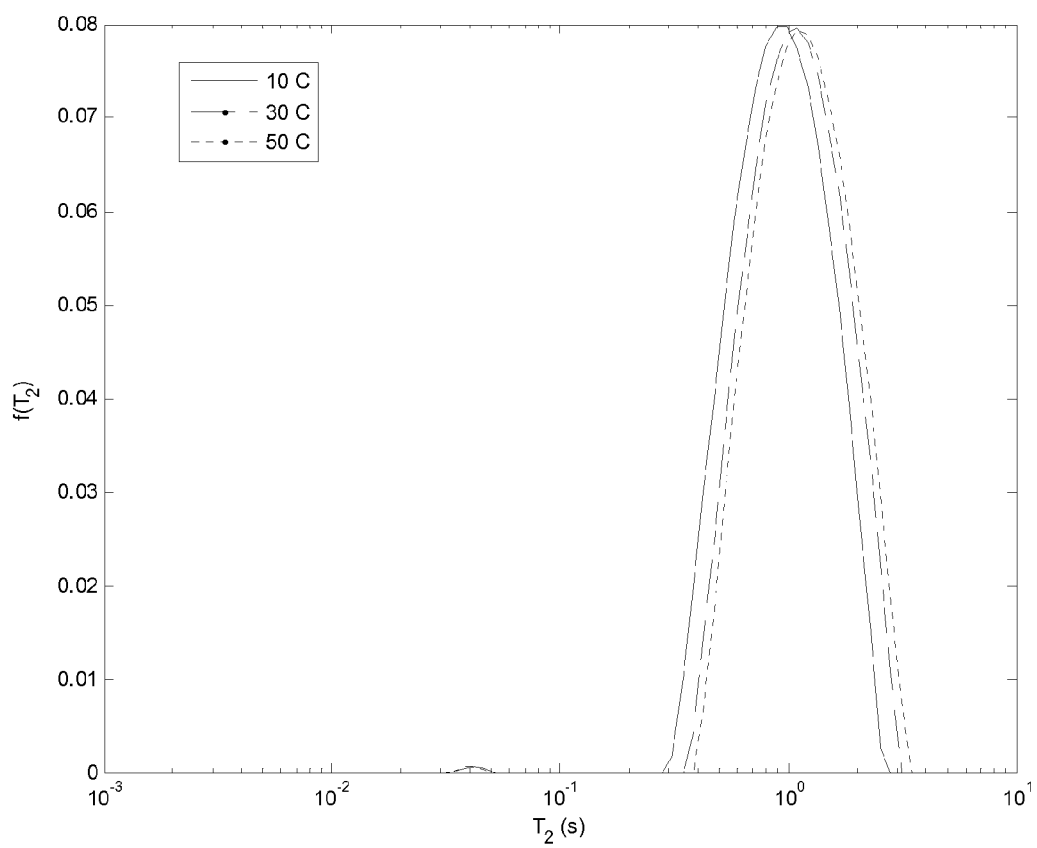
FIG. 9 represents $T_2$ distributions obtained for data shown in FIG. 1 using inverse Laplace transform with regularization described in equation (6).
Figure 10:
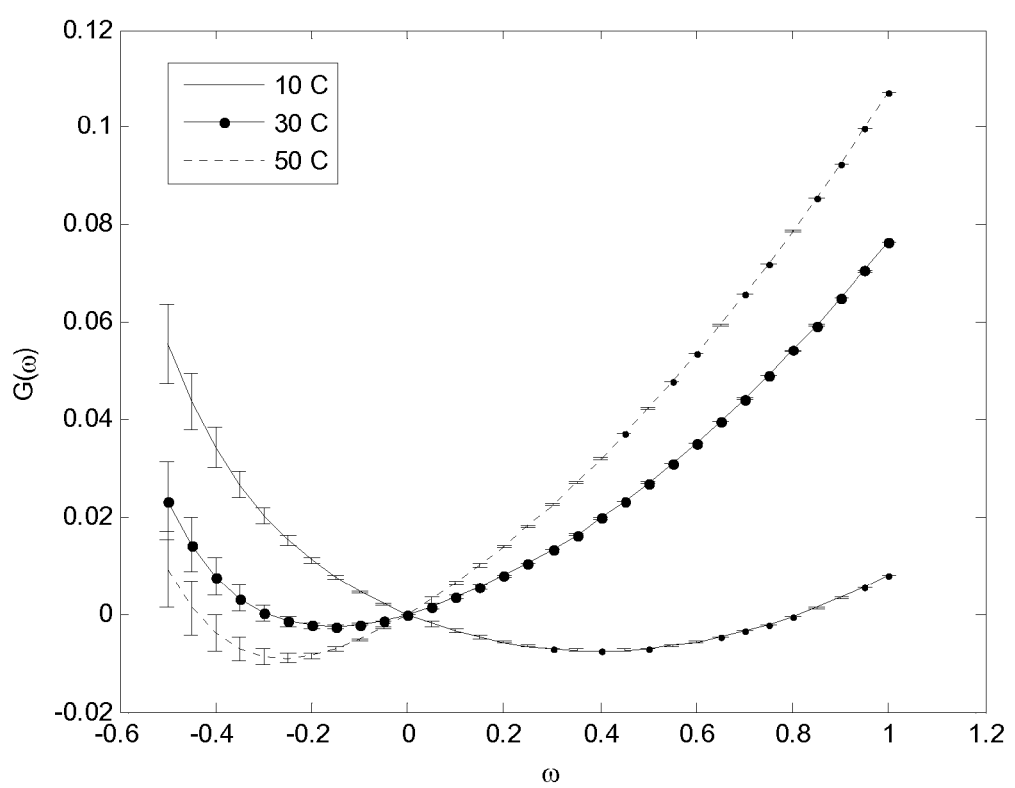
FIG. 10 represents moments obtained for data shown in FIG. 1 using equations. (3)-(7)

The simulation model parameters are shown in columns 1-3 in Table 3. The simulated magnetization data are analyzed using two methods: the traditional inverse Laplace transform described in [6] and the new analysis. The resultant $T_2$ distributions obtained from the traditional method are shown in FIG. 9. Column 4 in Table 3 provides the results of the analysis using this method. The error-bars were obtained using Monte-Carlo analysis with a number of simulated data sets with different noise realizations. Comparing column 4 with column 3, we see that the parameters $\langle \ln(T_2) \rangle$ and κ are biased, and associated with a large variance. This bias results from estimated $T_2$ distributions that have been artificially smoothened by regularization. Artificial peaks at smaller and larger relaxation times also contribute significantly to the bias and variance. FIG. 10 shows the moments obtained by the new analysis. Column 5 in Table 3 provides the quantitative results on the data. By comparing columns 3 and 5, it is seen that the new analysis performs reasonably well. The parameters are estimated within a tolerable bias and variance.

TABLE 3

Simulation 1: Comparison of results indicates that the new analysis performs better than the traditional approach.

| Model Parameters | Temp(C.) | True Values | Inv. Laplace Transform | New Analysis |
|---|---|---|---|---|
| $\langle \log_{10}(T_2) \rangle$ | 10 | −0.036 | −0.04 ± 0.01 | −0.037 ± 0.002 |
| | 30 | 0.032 | 0.023 ± 0.01 | 0.032 ± 0.002 |
| | 50 | 0.062 | 0.053 ± 0.01 | 0.061 ± 0.002 |
| $\sigma_{\log 10(T_2)}^2$ | 10 | 0.2 | 0.25 ± 0.06 | 0.198 ± 0.003 |
| | 30 | 0.2 | 0.25 ± 0.06 | 0.199 ± 0.003 |
| | 50 | 0.2 | 0.25 ± 0.06 | 0.200 ± 0.003 |
| κ | 10 | 1.24 | 1.54 ± 0.35 | 1.23 ± 0.02 |
| | 30 | 1.24 | 1.55 ± 0.37 | 1.24 ± 0.02 |
| | 50 | 1.24 | 1.56 ± 0.38 | 1.24 ± 0.03 |

Figure 11:
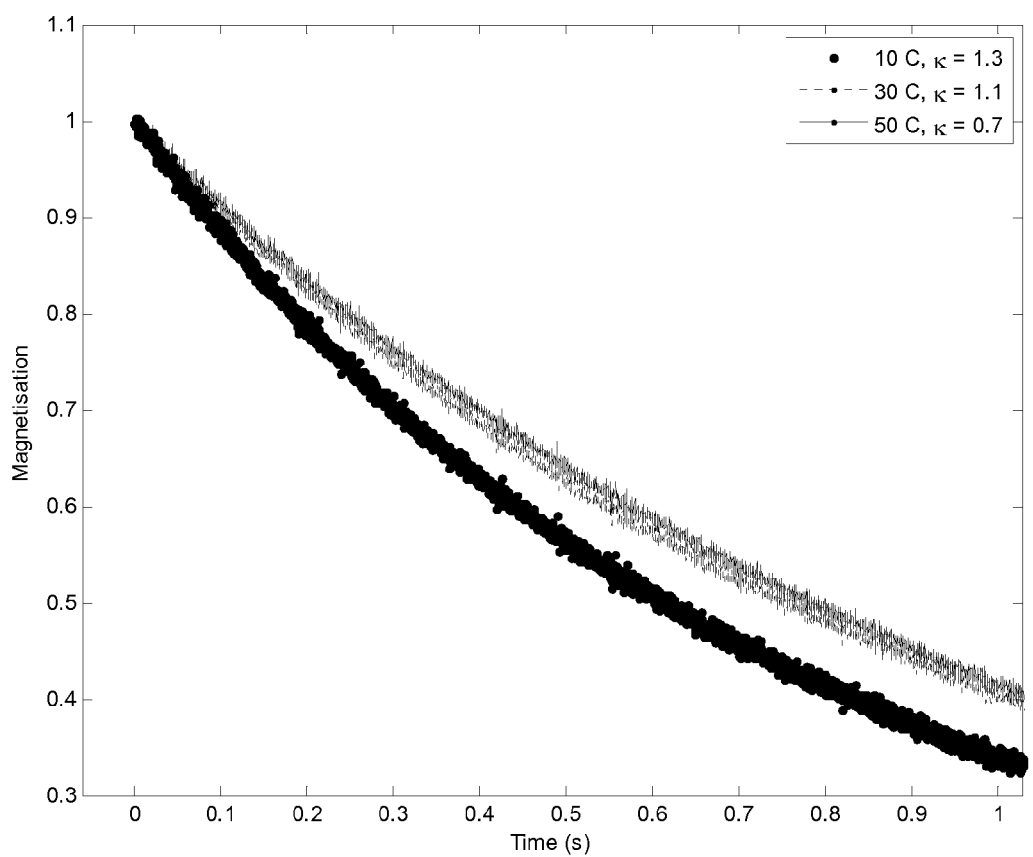
FIG. 11 represents magnetization data simulated with additive white noise with $\sigma_\epsilon = 0.01$ at three different temperatures.
Figure 12:
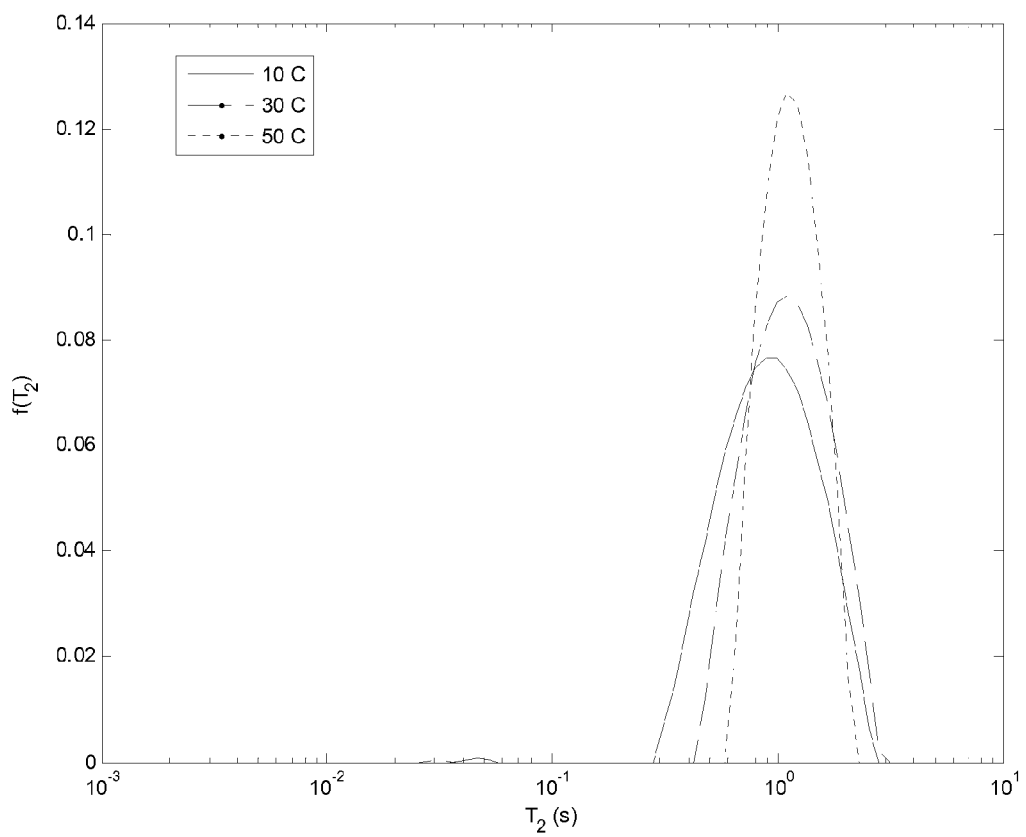
FIG. 12 shows $T_2$ distributions obtained for data shown in FIG. 4 using inverse Laplace transform with regularization described in equation (6).
Figure 13:
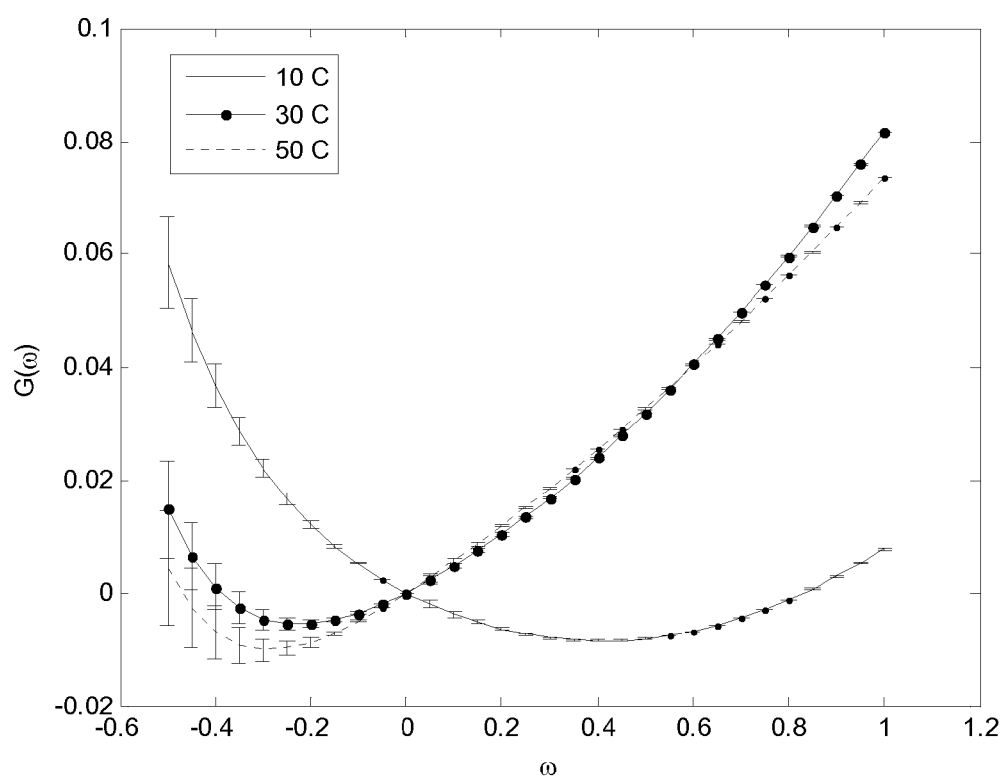
FIG. 13 shows moments obtained for data shown in FIG. 4 using equations. (3)-(7).

In a second simulation, data were simulated from the same gas chromatography as the previous example of FIG. 8 with the exception that κ decreases with increasing temperature as shown in column 3 in Table 4. The data are corrupted with white Gaussian noise and shown in FIG. 11. The results of the analysis using the traditional inverse Laplace transform are shown in FIG. 12 and column 4 in Table 4. The results of the new analysis are shown in FIG. 13 and column 5. As before, the error-bars were obtained from Monte-Carlo analysis with a number of simulated data sets with different noise realizations. Comparing columns 3 and 5, it is seen that the new analysis performs better than the inverse Laplace transform; all the parameters have a smaller bias and variance. Further, the trend in κ with temperature is also estimated reasonably well.

TABLE 4

Simulation 2: Comparison of results indicates that the new analysis performs better than the traditional approach.

| Model Parameters | Temp(C.) | True Values | Inv. Laplace Transform | New Analysis |
|---|---|---|---|---|
| $\langle \log_{10}(T_2) \rangle$ | 10 | −0.040 | −0.05 ± 0.01 | −0.040 ± 0.002 |
| | 30 | 0.046 | 0.04 ± 0.01 | 0.040 ± 0.002 |
| | 50 | 0.057 | 0.052 ± 0.01 | 0.056 ± 0.002 |
| $\sigma_{\log 10(T_2)}^2$ | 10 | 0.21 | 0.26 ± 0.06 | 0.21 ± 0.003 |
| | 30 | 0.18 | 0.22 ± 0.06 | 0.18 ± 0.004 |
| | 50 | 0.11 | 0.16 ± 0.06 | 0.12 ± 0.005 |

TABLE 4-continued

Simulation 2: Comparison of results indicates that the new analysis performs better than the traditional approach.

| Model Parameters | Temp(C.) | True Values | Inv. Laplace Transform | New Analysis |
|---|---|---|---|---|
| κ | 10 | 1.3 | 1.58 ± 0.34 | 1.28 ± 0.02 |
|   | 30 | 1.1 | 1.43 ± 0.39 | 1.11 ± 0.02 |
|   | 50 | 0.7 | 1.50 ± 0.38 | 0.75 ± 0.03 |

According to embodiment of the invention, moments of the relaxation time and/or diffusion can be directly computed from the measured magnetization data. In turn, these moments are directly related to properties of a sample like the petrophysical parameters such as $\langle \ln(T_2) \rangle$ and $\sigma_{\ln(T_2)}$. The moments can also directly provide fluid parameters such as the mean chain length $\overline{N}$ and viscosity $\eta$. Given NMR and Gas Chromatography data, other parameters that relate fluid composition to relaxation or diffusion data can also be estimated. The error-bars in the estimated parameters can also be readily computed. In addition, monitoring of some of these fluid parameters with changes in temperature and pressure can be an indicator of phase transitions in the hydrocarbon.

In this section, we show that the function $G(\omega)$ defined in eqn. (3) is the second characteristic function of $T_2$. From eqn. (4), we can see that the function $G(\omega)=0$ when $\omega=0$.

$$G(\omega = 0) = \ln\langle T_2^{\omega=0}\rangle \equiv \ln\left[\frac{\int_0^\infty T_2^{\omega=0} f_{T_2}(T_2) dT_2}{\int_0^\infty f_{T_2}(T_2) dT_2}\right] = 0 \quad (20)$$

Next, eqn. (4) can be re-written as, $$\langle T_2^\omega \rangle \equiv \frac{\int_0^\infty e^{\omega \ln(T_2)} f_{T_2}(T_2) dT_2}{\int_0^\infty f_{T_2}(T_2) dT_2} \quad (21)$$

$$= \frac{\int_{-\infty}^\infty e^{\omega \ln(T_2)} f_{\ln(T_2)}(\ln(T_2)) d\ln(T_2)}{\int_{-\infty}^\infty f_{\ln(T_2)}(\ln(T_2)) d\ln(T_2)}$$

where $f_{\ln(T_2)}$ refers to the underlying density function of $\ln(T_2)$. Thus $$\frac{dG(\omega)}{d\omega} = \frac{d\ln\langle T_2^\omega \rangle}{d\omega} = \frac{\int_{-\infty}^\infty \ln(T_2) e^{\omega \ln(T_2)} f_{\ln(T_2)}(\ln(T_2)) d\ln(T_2)}{\int_{-\infty}^\infty e^{\omega \ln(T_2)} f_{\ln(T_2)}(\ln(T_2)) d\ln(T_2)} \quad (22)$$

and $$\frac{d^2 G(\omega)}{d\omega^2} = \frac{d^2 \ln\langle T_2^\omega \rangle}{d\omega^2} \quad (23)$$

$$= \frac{\int_{-\infty}^\infty [\ln(T_2)]^2 e^{\omega \ln(T_2)} f_{\ln(T_2)}(\ln(T_2)) d\ln(T_2)}{\int_{-\infty}^\infty e^{\omega \ln(T_2)} f_{\ln(T_2)}(\ln(T_2)) d\ln(T_2)} -$$

$$\left(\frac{\int_{-\infty}^\infty \ln(T_2) e^{\omega \ln(T_2)} f_{\ln(T_2)}(\ln(T_2)) d\ln(T_2)}{\int_{-\infty}^\infty e^{\omega \ln(T_2)} f_{\ln(T_2)}(\ln(T_2)) d\ln(T_2)}\right)^2$$

Therefore, $$\left.\frac{dG}{d\omega}\right|_{\omega=0} = \langle \ln(T_2) \rangle, \quad \left.\frac{d^2 G}{d\omega^2}\right|_{\omega=0} = \sigma^2_{\ln(T_2)} \quad (24)$$

Similarly, higher-order moments or cumulants of $\ln(T_2)$ are obtained by taking the higher-order derivatives of $G(\ )$ with respect to $\omega$.

Appendix B

In this section, we show that moments of $\ln(T_2)$ defined in eqn. (4) can be computed directly from the measurement, from the definition of $\Gamma(.)$ function. Consider the following two cases.

Case 1: When $\omega>0$. The $\Gamma(.)$ function is a generalization of the factorial function and is defined as, $$\Gamma(\omega) \equiv \int_0^\infty t^{\omega-1} e^{-t} dt \quad (25)$$

Therefore, when the operator $t^{\omega-1}$ operates on a single exponential $e^{-at}$ where $a>0$, $$\int_0^\infty t^{\omega-1} e^{-at} dt = \frac{\Gamma(\omega)}{a^\omega} \quad (26)$$

When the operator $t^{\omega-1}$ operates on a sum of exponentials given by eqn. (1), then, $$\int_0^\infty t^{\omega-1} M(t) dt = \int_0^\infty t^{\omega-1} \int_0^\infty e^{-t/T_2} f_{T_2}(T_2) dT_2 dt \quad (27)$$

$$= \int_0^\infty \left[\int_0^\infty t^{\omega-1} e^{-t/T_2} dt\right] f_{T_2}(T_2) dT_2$$

$$= \Gamma(\omega) \int_0^\infty T_2^\omega f_{T_2}(T_2) dT_2$$

From eqns. (4) and (27), $$\langle T_2^\omega \rangle = \frac{1}{\Gamma(\omega)\phi} \int_0^\infty t^{\omega-1} M(t) dt \quad (28)$$

Case 2: When $\omega \le 0$.
Consider the integrand $$t^{\mu-1} \frac{d^n M}{dt^n}$$

where $n \ge 0$ is an integer and $0 < \mu \le 1$. Let $\omega = \mu - n$. From eqn. (1), $$\int_0^\infty t^{\mu-1} \left[ \frac{d^n M(t)}{dt^n} \right] dt = (-1)^n \int_0^\infty \left[ \int_0^\infty \frac{t^{\mu-1}}{T_2^n} e^{-t/T_2} \right] f_{T_2}(T_2) dT_2 \qquad (29)$$

$$= (-1)^n \Gamma(\mu) \langle T_2^{\mu-n} \rangle \phi$$

$$= (-1)^n \Gamma(\mu) \langle T_2^\omega \rangle \phi$$

Thus $$\langle T_2^\omega \rangle = \frac{(-1)^n}{\Gamma(\mu)\phi} \int_0^\infty t^{\mu-1} \left[ \frac{d^n M(t)}{dt^n} \right] dt \qquad (30)$$

Figure 14:
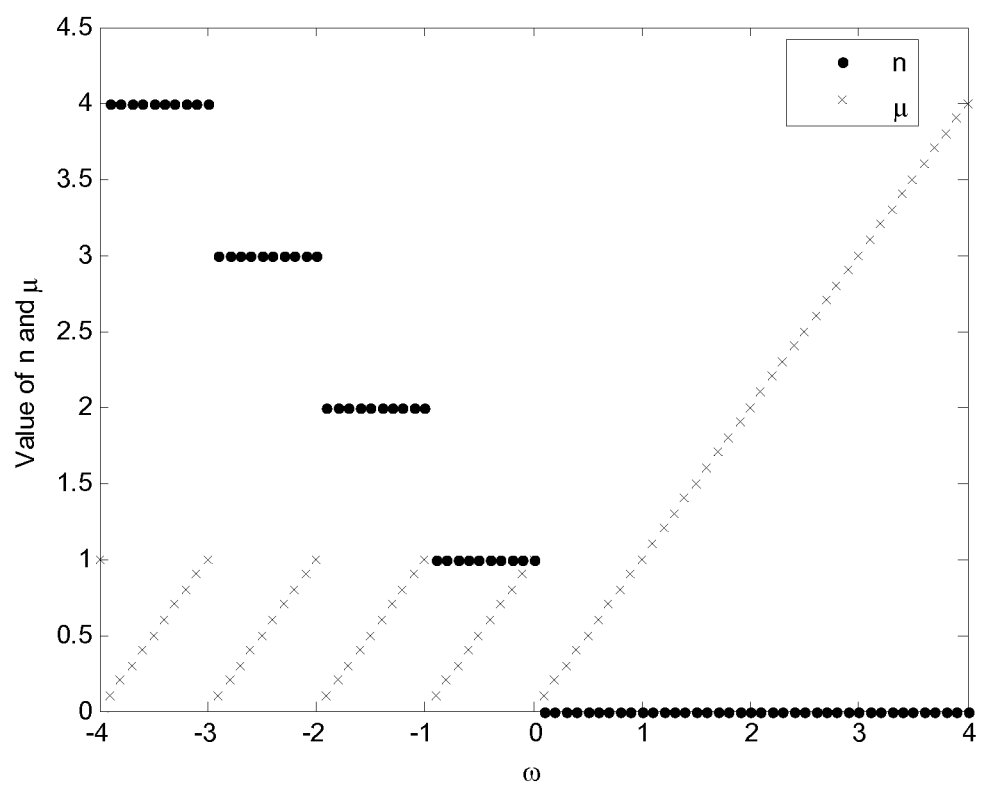
FIG. 14 represents for given ω that the values of n and μ are unique and determined by eqn. (7).

Given a value of $\omega \leq 0$, there are a number of different ways to compute $\mu$ and n such that the equation $\omega = \mu - n$ where n is an integer is valid. One of these methods is to choose n and $\mu$ such that $$n = [-\omega] + 1 \text{ and } 0 < \mu \leq 1 \qquad (31)$$

where $[\omega]$ refers to the integral part of real number $\omega$. Using integration by parts, it can be shown that all the other methods of choosing n and $\mu$ collapse to eqn. (31). FIG. 14 shows the variation of n and $\mu$ for the different values of $\omega$.

In another aspect of the invention, porosity can also be estimated directly from the measured data. Let $R(\omega) = \phi \langle T_2^\omega \rangle$. From eqn. (6), $$R(\omega) = \frac{(-1)^n}{\Gamma(\mu)} \int_0^\infty t^{\mu-1} \left[ \frac{d^n M(t)}{dt^n} \right] dt, \mu - n = \omega \qquad (32)$$

where the relation between n, $\mu$ and $\omega$ is given in eqn. (7).

By definition in eqn. (4), $\langle T_2^{\omega=0} \rangle = 1$. Therefore, the porosity can be computed as $\phi = R(\omega=0)$, which corresponds to $\mu = n = 1$.

Appendix C

In this section, we show another embodiment of the invention to compute the moments of relaxation time and/or diffusion. This embodiment takes advantage of the fact that the Fourier transform of a Gaussian is a Gaussian with a width in the Fourier domain that is inversely proportional to the width in the time domain. The moments can be computed directly from the data, $$\langle T_2^\omega \rangle = \begin{cases} \frac{1}{\Gamma(\omega)\phi} \int_0^\infty t^{\omega-1} M(t) dt & \text{if } \omega > 0 \\ \frac{2\pi^{(0.5-2\omega)}}{\Gamma(0.5-\omega)\phi} \int_0^\infty k^{-2\omega} \tilde{M}_y(k) dk & \text{if } \omega < 0.5 \end{cases} \qquad (33)$$

where $\tilde{M}_y(k)$ is the Fourier transform of the measured data in $\sqrt{t}$ domain, $$\tilde{M}_y(k) = \int_{-\infty}^\infty M_y(y) e^{-2\pi i k y} dy, \text{ where } M_y(y) = M(t = y^2) \qquad (34)$$

The proof of eqns. (33) and (34) is given below.

Case 1: When $\omega > 0$: The proof of the first part of eqn. (33) is given in eqns. (25)-(28) in Appendix B.

Case 2: When $\omega < 0.5$: The proof of this section depends on the following eqns. (35)-(38). Using eqn. (25), it is seen that $$\int_0^\infty t^{\mu-1} e^{-t^2} dt = \frac{1}{2} \Gamma(\mu/2) \text{ when } \mu > 0 \qquad (35)$$

Therefore, for any a>0 and $\mu > 0$, $$\int_0^\infty t^{\mu-1} e^{-at^2} dt = \frac{1}{2a^{\mu/2}} \Gamma(\mu/2) \qquad (36)$$

Let $\tilde{F}(k)$ denote the Fourier transform of a function $f(t)$, $$\tilde{F}(k) = \int_{-\infty}^\infty f(t) e^{-2\pi i k t} dt \qquad (37)$$

The Fourier transform of a Gaussian is a Guassian with a width in the frequency domain that is inversely proportional to the width in the time domain. Thus when $$f(t) = e^{-ct^2}, \text{ then } \tilde{F}(k) = \sqrt{\frac{\pi}{c}} e^{-\frac{\pi^2 k^2}{c}} \qquad (38)$$

Let $M_y(y) = M(t=y^2)$ where $M(t)$ is the measured data given in eqn. (1), $$M_y(y) = \int_0^\infty e^{-\frac{y^2}{T_2}} f_{T_2}(T_2) dT_2. \qquad (39)$$

Let $\tilde{M}_y(k)$ denote the Fourier transform of $M_y$, $$\tilde{M}_y(k) = \int_{-\infty}^\infty M_y(y) e^{-2\pi i k y} dy \qquad (40)$$

From eqns. (39) and (40), $$\tilde{M}_y(k) = \int_0^\infty \left[ \int_{-\infty}^\infty e^{-\frac{y^2}{T_2}} e^{-2\pi i k y} dy \right] f_{T_2}(T_2) dT_2 \qquad (41)$$

Using eqns. (38) and (41)

$$\tilde{M}_y(k) = \sqrt{\pi} \int_0^\infty \sqrt{T_2} e^{-\pi^2 k^2 T_2} f_{T_2}(T_2) dT_2 \qquad (42)$$

Now, $$\int_0^\infty k^{\mu-1} \tilde{M}_y(k) dk = \sqrt{\pi} \int_0^\infty \left[ \int_0^\infty k^{\mu-1} e^{-\pi^2 k^2 T_2} dk \right] \sqrt{T_2} f(T_2) dT_2 \qquad (43)$$

Using eqns. (36) with $a = \pi^2 T_2$ and (43)

$$\int_0^\infty k^{\mu-1} \tilde{M}_y(k) dk = \frac{(\pi)^{0.5-\mu} \Gamma(\mu/2)}{2} \langle T_2^{0.5(1-\mu)} \rangle \phi \text{ when } \mu > 0 \qquad (44)$$

Let $0.5(1-\mu)=\omega$. When $\mu>0$, $\omega<0.5$. Therefore, for $\omega<0.5$ $$\langle T_2^\omega \rangle = \frac{2\pi^{(0.5-2\omega)}}{\Gamma(0.5-\omega)\phi} \int_0^\infty k^{-2\omega} \tilde{M}_y(k) dk \qquad (45)$$

where $\tilde{M}_y$ is the Fourier transform of the magnetization data $M_y$ in eqn. (40) and $M_y$ is the magnetization data in the $\sqrt{t}$ domain.

In another aspect of the invention, porosity can also be estimated directly from the measured data in the Fourier domain. Let $R(\omega)=\phi\langle T_2^\omega \rangle$. From eqn. (45), $$R(\omega=0) = \phi = \frac{2\sqrt{\pi}}{\Gamma(0.5)} \int_0^\infty \tilde{M}_y(k) dk \qquad (46)$$

A new mathematical formulation is described where the moments of a random variable can be directly computed from the measurement. The method has two distinct advantages: the computation of moments is linear and does not require prior knowledge or information of the expected distribution. A moment of a random variable x with density function $f_x(x)$ is defined as, $$\langle x^\omega \rangle \equiv \frac{\int_0^\infty x^\omega f_x(x) dx}{\int_0^\infty f_x(x) dx} \qquad (6)$$

For NMR applications, the variable x corresponds to relaxation times $T_1$, $T_2$, or diffusion D. The moments of relaxation times or diffusion can be directly computed from the measured magnetization data, $$\langle x^\omega \rangle = \frac{(-1)^n}{\Gamma(\mu)\phi} \int_0^\infty t^{\mu-1} \left[ \frac{d^n M(t)}{dt^n} \right] dt, \omega = \mu - n \qquad (7)$$

where $\Gamma(\ )$ represents the Gamma function and $$\phi = M(t=0) = \int_0^\infty f_x(x) dx.$$

The contribution of variable $\omega$ is in two parts: a real number $\mu$ and an integer n where the mathematical operator $t^{\mu-1}$ operates on the n-th derivative of the data. Given a value of $\omega$, the values of n and $\mu$ are unique and given as, $$\omega > 0: n=0, \mu=\omega$$

$$\omega \leq 0: \omega = \mu - n, \ 0 < \mu \leq 1, \ n = \lfloor -\omega \rfloor + 1 \qquad (8)$$

where $[\omega]$ refers to the integral part of real number $\omega$. FIG. 1 is a plot 110 showing the values of n and $\mu$ for different values of $\omega$ as determined by above these equations.

According to some embodiments, the computation of moments of relaxation times $T_1$, $T_2$, or diffusion D, in conjunction with the scaling laws, can lead to greatly improved alternative pulse sequences to specifically target or estimate only certain moments of relaxation time/diffusion. In co-pending U.S. Patent Application Publication No. 2008-0314582 (incorporated herein by reference), "targeted" measurements are described as measurements that target a certain specified parameter at a particular location in the reservoir space. These targeted measurements are achieved by both hardware and software modifications.

According to some embodiments, the concept of targeted measurements is applied to NMR data and alternate pulse sequences are described to directly estimate the moments of relaxation time or diffusion coefficients. According to some embodiments, alternate pulse sequences are designed by taking advantage of the specific exponential-kernel structure in eqn. (1) as well as the computation of moments using eqn. (7). The magnetization data from the new pulse sequences can be directly interpreted to obtain fluid properties.

According to some embodiments, further detail will now be provided for modified pulse sequences for measuring NMR data. The non-uniformly spaced pulse sequences are targeted to specifically measure one of the moments of the relaxation time $T_1$, $T_2$, or D distribution. For simplicity, consider that the random variable in eqn. (1) is $T_1$ and a specific $\omega$-th moment of $T_1$ is desired, where $\omega > 0$. This corresponds to the right-hand side of the $\omega$ axis in FIG. 1. In this case, from eqns. (7) and (8), $$\langle T_1^\omega \rangle = \frac{1}{\Gamma(\omega)\phi} \int_0^\infty t^{\omega-1} M(t) dt \qquad (9)$$

We introduce a new variable where $$\tau = t^\omega \qquad (10)$$

Therefore, eqn. (9) can be re-written as $$\langle T_1^\omega \rangle = \frac{1}{\Gamma(\omega+1)\phi} \int_0^\infty M_\tau(\tau) d\tau \qquad (11)$$

where $M_\tau(\tau)$ is the magnetization data in the $\tau$ domain. Eqn. (11) indicates that if the data are acquired such that they are uniformly spaced in the $\tau$ domain, then the sum of the measured data directly provides the $\omega$-th moment. From eqn. (10), uniform spacing in the $\tau$ domain implies non-uniform spacing in the time (t) domain.

Figure 2:
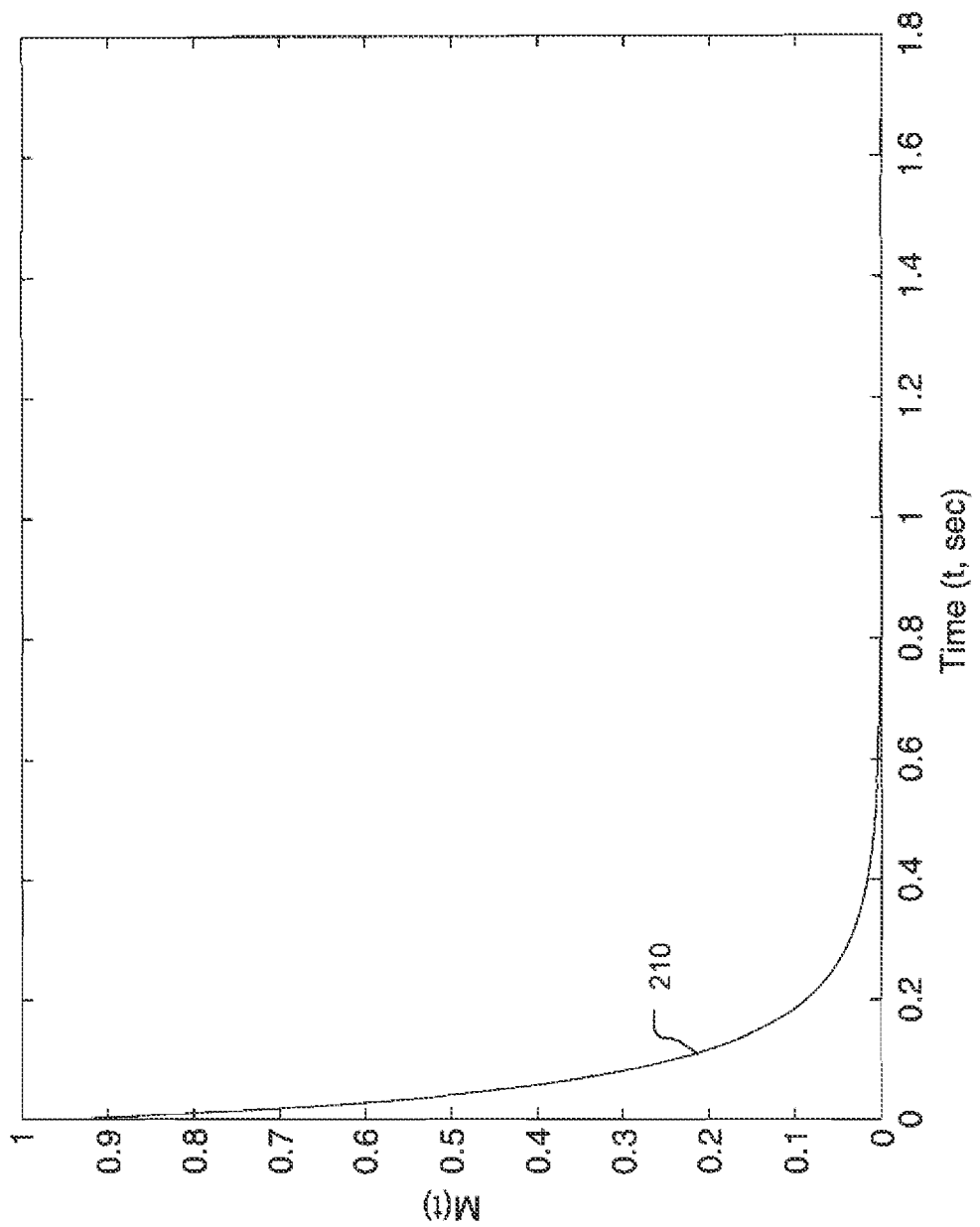
FIG. 2 is a plot showing an example of a single exponential acquired at uniform time intervals in the time-domain.
Figure 3:
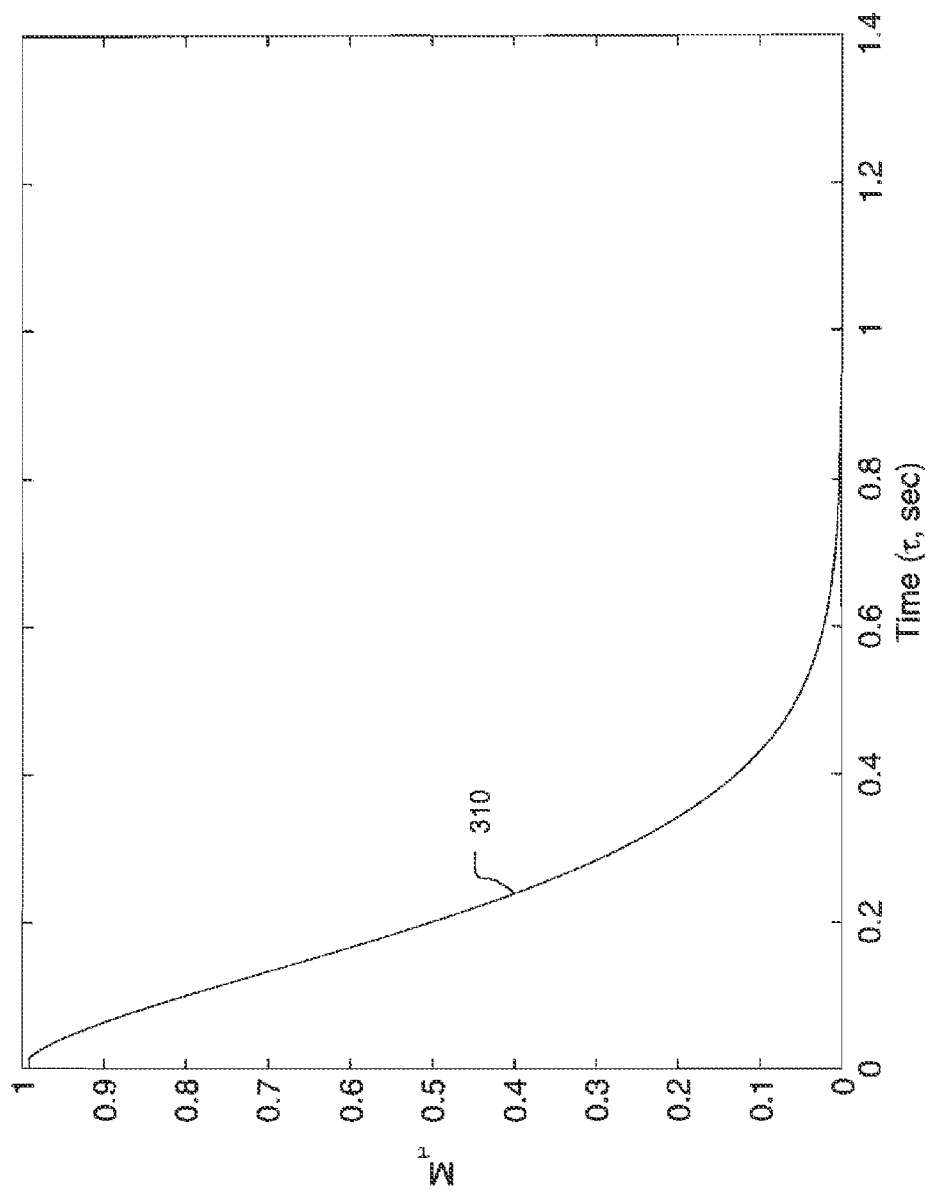
FIG. 3 is a plot showing a non-uniform sampling, according to some embodiments.
Figure 4:
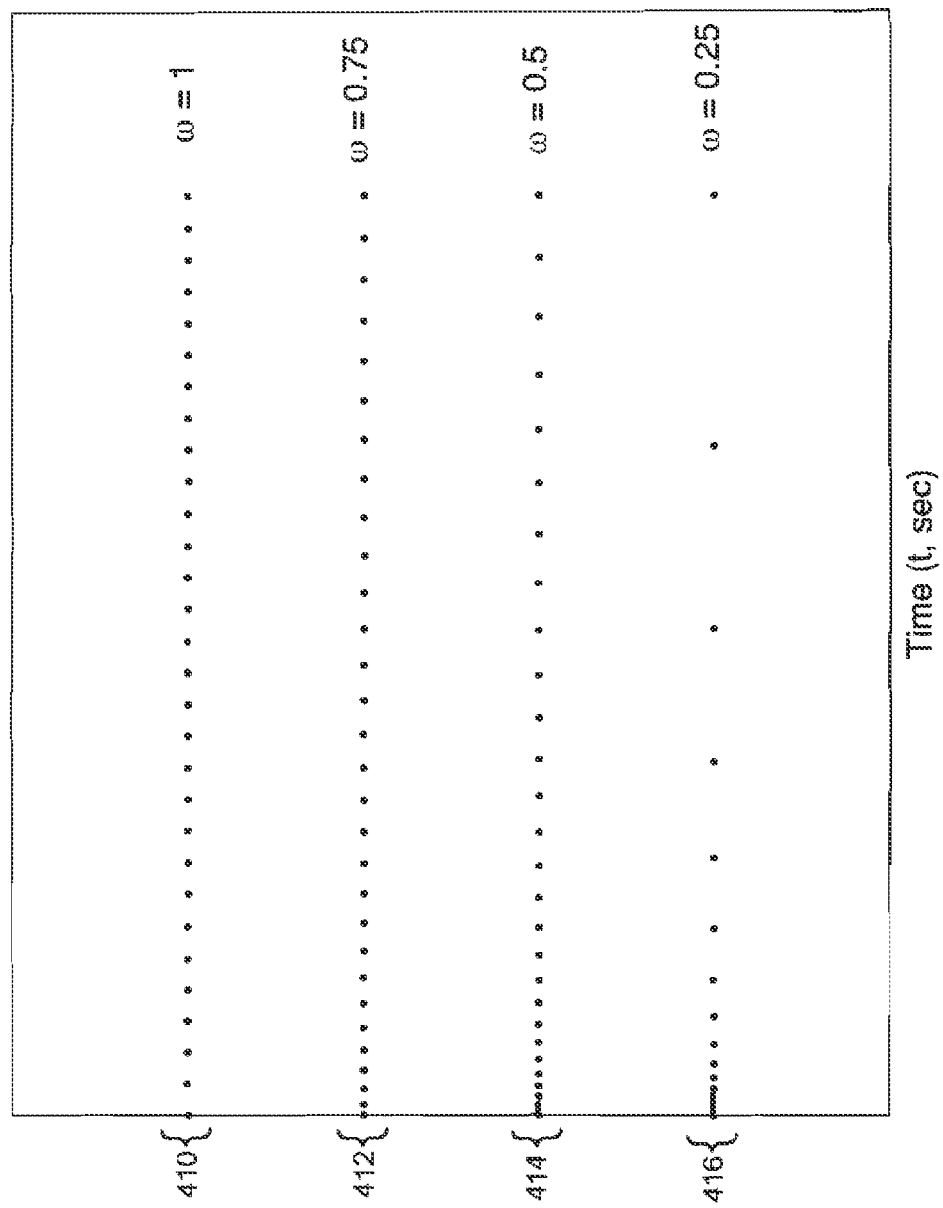
FIG. 4 plots examples of non-uniform sampling in time domain that can directly provide moments of relaxation or diffusion distribution, according to some embodiments.

We illustrate this with an example. FIG. 2 is a plot showing an example of a single exponential acquired at uniform time intervals in the time-domain. In particular, curve 210 plots a single exponential decay of the form $M(t)=e^{-t/T_1}$ in the time-domain as shown in where the data are uniformly sampled in time. In this example, suppose that the 0.5-th moment of $T_1$ is required. FIG. 3 is a plot showing a non-uniform sampling, according to some embodiments. In particular, using eqn. (10), the data shown by curve 310 are sampled uniformly in the $\sqrt{t}$ domain. Curve 310 is an example of a single exponential in the time-domain into a Guassian in the $\tau$ domain with $M(t)=e^{-\tau^2/T_1}$. Using eqn. (11), the sum of measured echoes of the Gaussian directly provides $\langle T_1^{0.5} \rangle$. Thus, if the $\omega$-th moment is desired, then the data need to be sampled non-uniformly in time according to eqn. (10). FIG. 4 plots examples of non-uniform sampling in time domain that can directly provide moments of relaxation or diffusion distribution, according to some embodiments. In particular, plots 410, 412, 414 and 416 represent sampling for w values of 1, 0.75, 0.5, and 0.25 respectively. When $0<\omega<1$, this leads to finer sampling at the initial part of the data and coarser sampling at the tail end of the data.

The concept of non-uniform sampling is also valid when $\omega<0$. Consider the case when $-1<\omega\leq 0$. In this case, eqn. (7) reduces to $$\langle T_1^\omega \rangle = \frac{-1}{\Gamma(\mu)\phi} \int_0^\infty t^{\mu-1}\left[\frac{dM(t)}{dt}\right]dt \text{ where } \mu = 1 + \omega > 0 \quad (12)$$

Eqn. (12) can be re-written as $$\langle T_1^\omega \rangle = \frac{-1}{\Gamma(\mu)\phi} \int_0^\infty t^{\mu-1}\left[\frac{d[M(t)-M(0)]}{dt}\right]dt \quad (13)$$

Using integration by parts, $$\langle T_1^\omega \rangle = \frac{-1}{\Gamma(\mu)\phi}[t^{\mu-1}\{M(t)-M(0)\}]_{t=0}^{t=\infty} - \quad (14)$$
$$\frac{(\mu-1)}{\Gamma(\mu)\phi}\int_0^\infty t^{\mu-2}[M(t)-M(0)]dt$$

$$= \frac{M(0)}{\phi}\delta_{\mu 1} + \frac{(\mu-1)}{\Gamma(\mu)\phi}\int_0^\infty t^{\mu-2}[M(t)-M(0)]dt \quad (15)$$

where $\delta_{\mu 1}=1$ only if $\mu=1$ and is zero otherwise. When $\mu=1$ (corresponding to $\omega=0$), the first term in eqn. (15) is 1 (since $M(0)=\phi$) and the second term is zero. This is consistent with the definition of the zero-th moment in eqn. (6) with $\langle T_1^{\omega=0} \rangle = 1$.

When $0<\mu<1$, the first term in eqn. (15) is zero. The second term is integrable at $t=0$ since $[M(t)-M(0)]\sim t$ as $t\to 0$. In this case, we introduce a new variable $\tau$ where $$\tau = t^{\mu-1} \quad (16)$$

Here, $\tau\to\infty$ when $t\to 0$, and $\tau\to 0$ when $t\to\infty$. Therefore, eqn. (15) becomes $$\langle T_1^\omega \rangle = \frac{-1}{\Gamma(\mu)\phi}\int_0^\infty [M_\tau(\tau) - M(0)]d\tau \quad (17)$$

Similar to eqn. (11), the area under the integrand $[M_T-M(0)]$ can be used to directly estimate the $\omega$-th moment. As shown herein below, the concept of the pulse sequence for $\omega>0$ and $-1<\omega\leq 0$ is valid for other ranges of $\omega$ as well. For example, when $-2<\omega\leq -1$, pulse sequences that directly measure the $\omega$-th moment are obtained by Taylor series expansion of the data with second-order terms in eqn. (13). Higher-order terms in the Taylor series lead to further negative values of $\omega$. As shown herein below, when $\omega$ is not a negative integer, $\langle T_1^\omega \rangle$ can be obtained by sampling uniformly in the $\tau$ domain, where $$\tau = t^\omega \quad (18)$$

When $\omega$ is a negative integer, from eqns. (7) and (8), the $\omega$-th moment is obtained by the $|\omega|$-th derivative of the data, $$\langle T_1^\omega \rangle = \frac{(-1)^{|\omega|}}{\phi}\frac{d^{|\omega|}M(t=0)}{dt^{|\omega|}} \quad (19)$$

In addition to computing the moments directly, this modified pulse sequence also enables fluid properties such as the average chain length and viscosity to be directly estimated in a simple manner. Re-writing eqns. (3) and (4), the average chain length and viscosity can be computed from moments of $T_1$ or $T_2$ relaxation time or diffusion, as $$\bar{N} = [B^{-1/\kappa}\langle T_1^{1/\kappa}\rangle]^{-\frac{\kappa}{\gamma+\kappa}} \quad (20)$$

$$\bar{N} = [A^{-1/\nu}\langle D^{1/\nu}\rangle]^{-\frac{\nu}{\nu+\beta}} \quad (21)$$

$$\eta \propto \langle D^{-1} \rangle \Rightarrow \eta \propto \left[\left|\langle T_1^{\frac{1}{\kappa}}\rangle\right|\right]^{\frac{\beta\kappa-\gamma\nu}{\gamma+\kappa}} \left\langle T_1^{-\frac{\nu}{\kappa}}\right\rangle \quad (22)$$

According to eqns. (20) and (21), the average chain length can be estimated from a modified pulse sequence to directly estimate the $(1/\kappa)$-th moment of relaxation time or $(1/\nu)$-th moment of diffusion. Similarly, viscosity can be estimated from two modified pulse sequences to directly estimate the $(1/\kappa)$-th and $(1/\nu)$-th moment of relaxation time. For diffusion data, the kernel in eqn. (1) is $e^{-Dt}$. Using eqn. (10) with $\omega=1$, the negative first moment of diffusion and viscosity are obtained.

In addition to directly providing the parameters of interest, these pulse sequences are optimized to estimate any desired moments of relaxation time and/or diffusion. In comparison to pulse sequences where the data is uniformly acquired in time, these pulse sequences can be used to acquire the data faster. For example, given $\omega>0$, the error-bar in the $\omega$-th moment of $T_1$ relaxation is, $$\sigma_{\langle T_1^\omega \rangle}\Big|_{Uniform\,Sampling} = \frac{\sigma_\epsilon}{\Gamma(\omega)\phi}t_E^\omega \sqrt{\sum_{n=1}^{N_e} n^{2\omega-2}} \quad (23)$$

Here $N_e$ denotes the total number of echoes obtained from uniform sampling between a given lower and upper limit of relaxation time and $t_E$ corresponds to the spacing between the echoes. In the case of non-uniform sampling, the error-bar in the $\omega$-th moment is, $$\sigma_{\langle T_1^\omega \rangle}\Big|_{Non-Uniform\,Sampling} = \frac{\sigma_\epsilon}{\Gamma(\omega+1)\phi}\tau_E\sqrt{N_e} \quad (24)$$

Here $\tau_E$ corresponds to the spacing between echoes in the $\tau$ domain. FIG. 5 is a plot showing the ratio of the error-bar in the moments obtained from uniform sampling to non-uniform sampling. There are two points to note from this curve 510. First, there is a significant advantage to non-uniform sampling as the error-bar in the computation of moments is lower (or at worst equal when $\omega=1$). Second, from eqns. (23) and (24), the standard deviation of noise for uniform sampling has to be smaller than that for non-uniform sampling to obtain a desired error-bar in the moments. Since the magnitude of the noise standard deviation in the data is inversely proportional to the square-root of the acquisition time, to achieve the same uncertainty in the parameter the data for non-uniform sampling can be acquired faster than that for uniform sampling.

Thus, according to some embodiments, a modified pulse sequence is provided that can directly provide moments of relaxation-time or diffusion distributions. This pulse sequence can be adapted to the desired moment of relaxation-time or diffusion coefficient. The data from this pulse sequence provides direct estimates of fluid properties such as average chain length and viscosity of a hydrocarbon. In general, in comparison with data acquired uniformly in time, this pulse sequence is faster and has a lower error bar in computing the fluid properties.

A general expression for the sampling rate of non-uniformly spaced pulse sequence will now be described in further detail, according to some embodiments. When $\omega$ is not a negative integer, $\langle T_1^\omega \rangle$ can be obtained by sampling uniformly in the $\tau$ domain, where $$\tau = t^\omega \quad (25)$$

Proof: For $\omega > 0$ and $1 < \omega < 0$, the proof has already been demonstrated in eqn. (11) and eqns. (12)-(17) respectively. When $-2 < \omega \leq 1$, from eqn. (8), n=2 and $\mu = \omega + 2$. In this case, from eqn. (7), $$\langle T_1^\omega \rangle = \frac{1}{\phi \Gamma(\mu)} \int_0^\infty t^{\mu-1} \frac{d^2}{dt^2} M(t) dt \quad (26)$$

$$= \frac{1}{\phi \Gamma(\mu)} \int_0^\infty t^{\mu-1} \frac{d^2}{dt^2} [M(t) - M(0) - tM^{(1)}(0)] dt$$

$$= \frac{1}{\phi \Gamma(\mu)} \left[ t^{\mu-1} \frac{d}{dt} \{M(t) - M(0) - tM^{(1)}(0)\} \right]_{t=0}^{t=\infty} -$$

$$\frac{(\mu-1)}{\phi \Gamma(\mu)} \int_0^\infty t^{\mu-2} \frac{d}{dt} [M(t) - M(0) - tM^{(1)}(0)] dt$$

$$= -\frac{1}{\phi} M^{(1)}(0) \delta_{\mu 1} -$$

$$\frac{1}{\phi \Gamma(\mu-1)} \left[ t^{\mu-2} \{M(t) - M(0) - tM^{(1)}(0)\} \right]_{t=0}^{t=\infty} +$$

$$\frac{(\mu-2)}{\phi \Gamma(\mu-1)} \int_0^\infty t^{\mu-3} [M(t) - M(0) - tM^{(1)}(0)] dt$$

$$= -\frac{1}{\phi} M^{(1)}(0) \delta_{\mu 1} +$$

$$\frac{(\mu-2)}{\phi \Gamma(\mu-1)} \int_0^\infty t^{\mu-3} [M(t) - M(0) - tM^{(1)}(0)] dt$$

$$= -\frac{1}{\phi} M^{(1)}(0) \delta_{\mu 1} +$$

$$\frac{1}{\phi \Gamma(\omega)} \int_0^\infty t^{\omega-1} [M(t) - M(0) - tM^{(1)}(0)] dt$$

where $\delta_{\mu 1} = 1$ only when $\mu = 1$ and is zero otherwise and $$M^1(t) = \frac{dM(t)}{dt}.$$

When $\mu=1$ (corresponding to $\omega=1$), the first term in eqn. (26) corresponds to the first derivative of the data at t=0 and is consistent with the definition of the negative first moment. In this case, the second term is zero. When $-2 < \mu < 1$, the first term in eqn. (26) is zero. The second term is integrable at t=0. Using eqn. (25), the area under the integrand $[M(t) - M(0) - tM^{(1)}(0)]$ can be used to directly estimate the $\omega$-th moment.

In general, when $n \geq 1$, eqn. (7) can be written as $$\langle T_1^\omega \rangle = \frac{(-1)^n}{\phi \Gamma(\mu)} \int_0^\infty t^{\mu-1} \frac{d^n}{dt^n} M(t) dt \quad (27)$$

$$= \frac{(-1)^n}{\phi \Gamma(\mu)} \int_0^\infty t^{\mu-1} M^{(n)}(t) dt$$

$$= \frac{(-1)^{n-1}}{\phi} M^{(n-1)}(0) \delta_{\mu 1} +$$

$$\frac{1}{\phi \Gamma(\mu-n)} \int_0^\infty t^{\mu-n-1} \left[ M(t) - \sum_{m=0}^{n-1} \frac{t^m}{m!} M^{(m)}(0) \right] dt$$

$$= \frac{(-1)^{n-1}}{\phi} M^{(n-1)}(0) \delta_{\mu 1} +$$

$$\frac{1}{\phi \Gamma(\omega)} \int_0^\infty t^{\omega-1} \left[ M(t) - \sum_{m=0}^{n-1} \frac{t^m}{m!} M^{(m)}(0) \right] dt$$

where $$M^{(m)}(t) = \frac{d^m}{dt^m} M(t) \quad (28)$$

and $$M^{(0)}(t) = M(t) \quad (29)$$

Note that:

$$M(t) - \sum_{m=0}^{n-1} \frac{t^m}{m!} M^{(m)}(0) \to t^n \text{ as } t \to 0 \quad (30)$$

As before, the first term in eqn. (27) is valid only for negative integer values of $\omega$ and corresponds to the $|\omega|$-th derivative of the data. For negative values of $\omega$ where $n < \omega < (n-1)$, the first term in eqn. (27) is zero. Using eqn. (25), the area under the integrand $$\left[ M(t) - \sum_{m=0}^{n-1} \frac{t^m}{m!} M^{(m)}(0) \right]$$

in the $\tau$ domain directly provides the $\omega$-th moment of relaxation time.

Figure 6A:
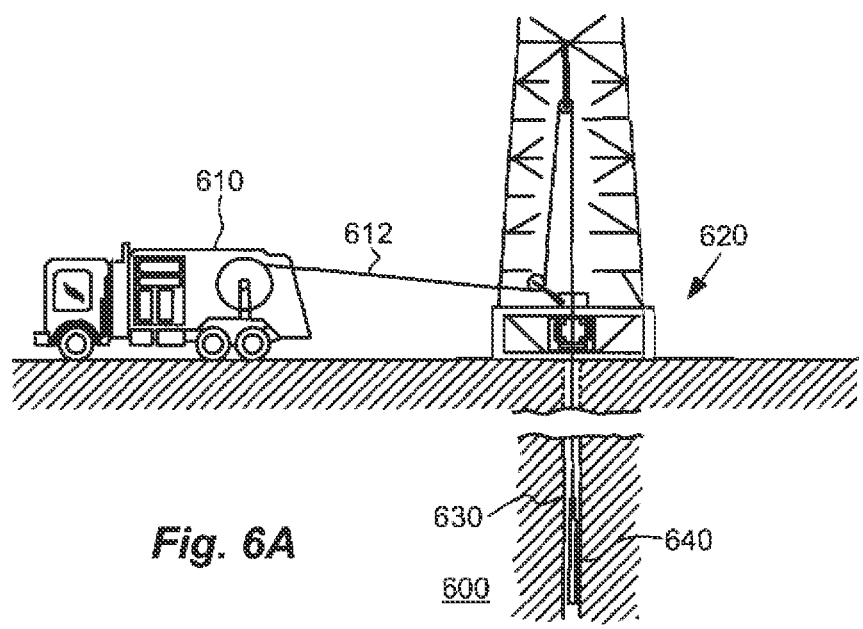
FIG. 6A shows an NMR tool being deployed in a wellbore, according to embodiments.

FIG. 6A shows an NMR tool being deployed in a wellbore, according to embodiments. Wireline truck 610 is deploying wireline cable 612 into well 630 via well head 620. Wireline tool 640 is disposed on the end of the cable 612 in a subterranean formation 600. Tool 640 includes an NMR tool, such as Schlumberger's Combinable Magnetic Resonance (CMR) Tool, or Schlumberger's MR Scanner Tool. According to some embodiments the NMR tool is combined with other downhole tools such as Schlumberger's Modular Formation Dynamics Tester downhole sampling tool. According to some embodiments, the NMR tool uses a pulse sequence as described herein. Data from the NMR tool can be recorded and/or processed downhole within tool 640, and/or can be transmitted to wireline truck 610 for recording and/or processing. According to embodiments, the NMR tool can be controlled, including the selection of pulse sequences, locally with processing systems within tool 640 and/or from the surface using processing systems for example in wireline truck 610.

Figure 6B:
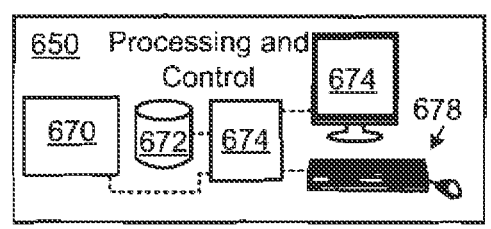
FIG. 6B is a schematic of a processing system used to control, record and process data from an NMR tool.

FIG. 6B is a schematic of a processing system used to control, record and process data from an NMR tool. Processing system 650 includes one or more central processing units 674, storage system 672, communications and input/output modules 670, a user display 676 and a user input system 678. Input/output modules 670 include modules to communicate with and control the NMR tool such that modified pulse sequences can be used as described herein.

Figure 7:
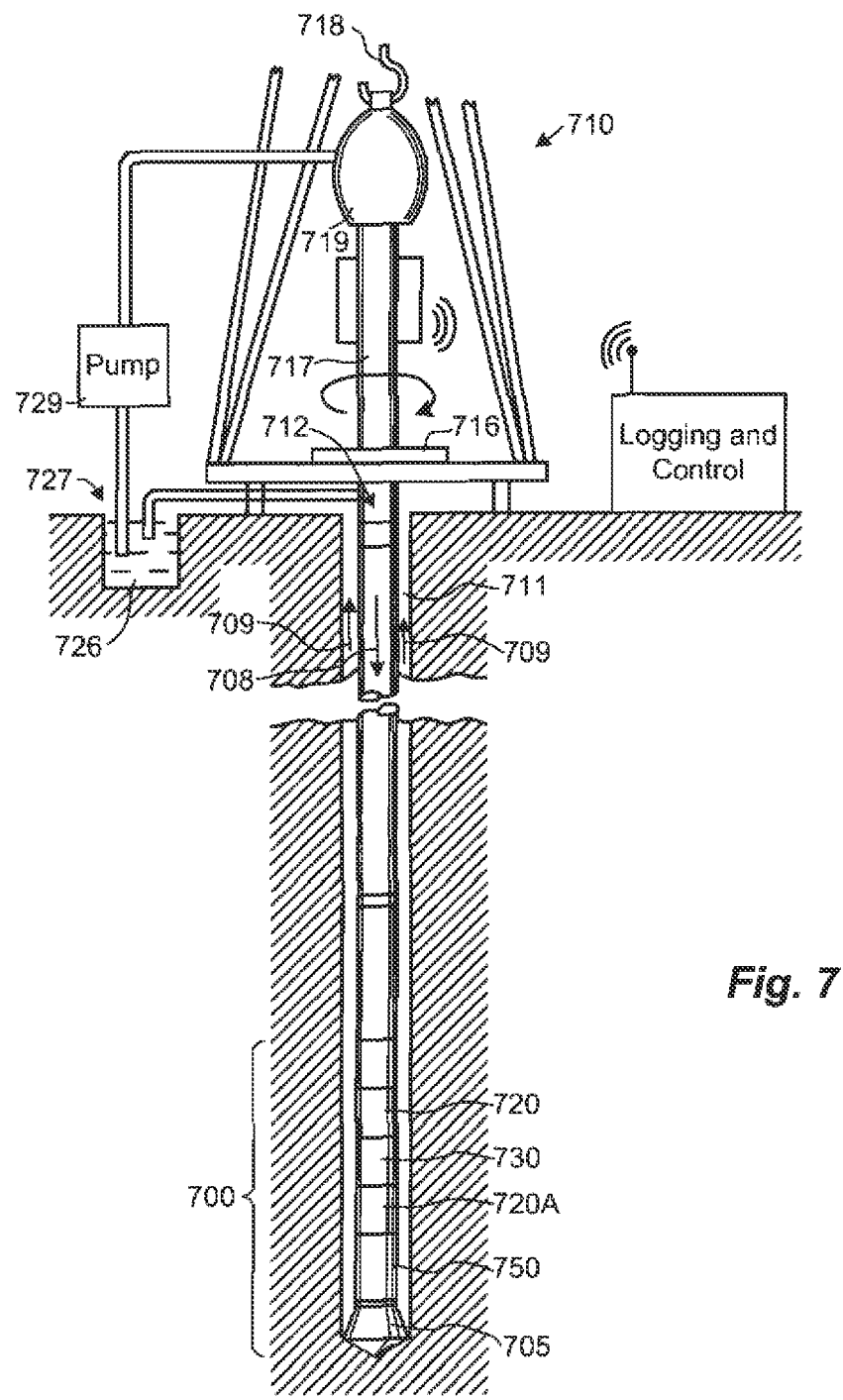
FIG. 7 illustrates another example of a wellsite system in which an NMR tool can be employed, according to some embodiments.

FIG. 7 illustrates another example of a wellsite system in which an NMR tool can be employed, according to some embodiments. The wellsite can be onshore or offshore. In this exemplary system, a borehole 711 is formed in subsurface formations by rotary drilling in a manner that is well known. Embodiments of the invention can also use directional drilling, as will be described hereinafter.

A drill string 712 is suspended within the borehole 711 and has a bottom hole assembly 700 which includes a drill bit 705 at its lower end. The surface system includes platform and derrick assembly 710 positioned over the borehole 711, the assembly 710 including a rotary table 716, kelly 717, hook 718 and rotary swivel 719. The drill string 712 is rotated by the rotary table 716, energized by means not shown, which engages the kelly 717 at the upper end of the drill string. The drill string 712 is suspended from a hook 718, attached to a traveling block (also not shown), through the kelly 717 and a rotary swivel 719 which permits rotation of the drill string relative to the hook. As is well known, a top drive system could alternatively be used.

In the example of this embodiment, the surface system further includes drilling fluid or mud 726 stored in a pit 727 formed at the well site. A pump 729 delivers the drilling fluid 726 to the interior of the drill string 712 via a port in the swivel 719, causing the drilling fluid to flow downwardly through the drill string 712 as indicated by the directional arrow 708. The drilling fluid exits the drill string 712 via ports in the drill bit 705, and then circulates upwardly through the annulus region between the outside of the drill string and the wall of the borehole, as indicated by the directional arrows 709. In this well known manner, the drilling fluid lubricates the drill bit 705 and carries formation cuttings up to the surface as it is returned to the pit 727 for recirculation.

The bottom hole assembly 700 of the illustrated embodiment a logging-while-drilling (LWD) module 720, a measuring-while-drilling (MWD) module 730, a roto-steerable system and motor, and drill bit 705.

The LWD module 720 is housed in a special type of drill collar, as is known in the art, and can contain one or a plurality of known types of logging tools. It will also be understood that more than one LWD and/or MWD module can be employed, e.g. as represented at 720A. (References, throughout, to a module at the position of 720 can alternatively mean a module at the position of 720A as well.) The LWD module includes capabilities for measuring, processing, and storing information, as well as for communicating with the surface equipment. In the present embodiment, the LWD module includes an NMR tool such as Schlumberger's ProVISION NMR tool.

The MWD module 730 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

According to some embodiments, the techniques described herein are applied to estimate properties from other types of excitations than NMR. For example the techniques can be applied to other types of data where excitations induce an exponential decay. According to some embodiments, the techniques are applied to inducing a non-uniform sequence of pressure changes in a material. According to some other embodiments, the techniques are applied to induce a non-uniform sequence of temperature changes in a material.

While many examples have been described herein with respect to designing interval spacings in the time domain, according to some embodiments, the techniques described herein are applied to interval spacings in other domains, such as designing interval spacings in the frequency domain.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A method to estimate properties of a material using nuclear magnetic resonance (NMR), the method comprising:
   performing an NMR measurement on the material using an NMR tool to apply an NMR pulse sequence to the material in a time-domain and to obtain time-domain exponentially decaying magnetization data for the material;
   determining a moment of a NMR distribution as a weighted linear combination of the time-domain exponentially decaying magnetization data using a processing system; and
   determining at least one property of the material using the moment of the NMR distribution using the processing system.

2. The method of claim 1, wherein the at least one property of the material comprises a petrophysical parameter.

3. The method of claim 2, wherein the petrophysical parameter comprises porosity.

4. The method of claim 1, wherein the at least one property of the material comprises a fluid parameter.

5. The method of claim 4, wherein the fluid parameter comprises at least one of mean chain length and viscosity.

6. The method of claim 4, further comprising:
  determining the fluid parameter of the material over time while at least one of pressure and temperature changes; and
  determining phase transitions within the material based on changes within the fluid parameter over time.

7. The method of claim 1, further comprising determining uncertainty in the moment of the NMR distribution from uncertainty in the time-domain exponentially decaying magnetization data.

8. The method of claim 1, further comprising determining uncertainty in the at least one property of the material from uncertainty in the moment of the NMR distribution.

9. The method of claim 1, wherein the moment of the NMR distribution comprises a moment of relaxation time.

10. The method of claim 1, wherein the moment of the NMR distribution comprises a moment of diffusion.

11. The method of claim 1, wherein the moment of the NMR distribution comprises more than one dimension.

12. The method of claim 11, wherein the moment of the NMR distribution comprises two dimensions.

13. The method of claim 1, wherein the moment of a NMR distribution is determined directly from the time-domain exponentially decaying magnetization data as weighted linear combination of the time-domain exponentially decaying magnetization data.

14. The method of claim 1, wherein the moment of a NMR distribution is determined without performing an inverse Laplace transform.

15. A method to estimate properties of a material using nuclear magnetic resonance (NMR), the method comprising:
  performing an NMR measurement on the material using an NMR tool to apply an NMR pulse sequence to the material in a time-domain and to obtain time-domain exponentially decaying magnetization data for the material;
  determining at least one of (i) a moment of relaxation time and (ii) a moment of diffusion as a weighted linear combination of the time-domain exponentially decaying magnetization data using a processing system; and
  determining at least one property of the material using the at least one of (i) the moment of relaxation time and (ii) the moment of diffusion using the processing system.

16. The method of claim 15, wherein the at least one property comprises at least one of porosity, mean chain length, and viscosity.

17. The method of claim 15, wherein the at least one of (i) a moment of relaxation time and (ii) a moment of diffusion is determined directly from the time-domain exponentially decaying magnetization data as weighted linear combination of the time-domain exponentially decaying magnetization data.

18. The method of claim 15, wherein the at least one of (i) a moment of relaxation time and (ii) a moment of diffusion is determined without performing an inverse Laplace transform.

19. A system to estimate properties of a material using nuclear magnetic resonance (NMR), the system comprising:
  a NMR tool configured to apply an NMR pulse sequence to the material in a time-domain and to obtain time-domain exponentially decaying magnetization data for the material;
  a processing system configured to (i) determine a moment of a NMR distribution as a weighted linear combination of the time-domain exponentially decaying magnetization data and (ii) determine at least one property of the material using the moment of the NMR distribution.

20. The system of claim 19, wherein the at least one property comprises at least one of porosity, mean chain length, and viscosity.

21. The system of claim 19, wherein the moment of the NMR distribution comprises a moment of relaxation time.

22. The system of claim 19, wherein the moment of the NMR distribution comprises a moment of diffusion.

23. The system of claim 19, wherein the moment of a NMR distribution is determined directly from the time-domain exponentially decaying magnetization data as weighted linear combination of the time-domain exponentially decaying magnetization data.

24. The system of claim 19, wherein the moment of a NMR distribution is determined without performing an inverse Laplace transform.

* * * * *